United States Patent
Dellis et al.

(10) Patent No.: US 11,280,746 B2
(45) Date of Patent: Mar. 22, 2022

(54) BACKGROUND SUPPRESSION FOR DOPPLER-FREE MM-WAVE SPECTROSCOPY

(71) Applicant: TEXAS INSTRUMENTS INCORPORATED, Dallas, TX (US)

(72) Inventors: Argyrios Dellis, McKinney, TX (US); Juan Herbsommer, Allen, TX (US); Adam Joseph Fruehling, Garland, TX (US)

(73) Assignee: TEXAS INSTRUMENTS INCORPORATED, Dallas, TX (US)

( * ) Notice: Subject to any disclaimer, the term of this patent is extended or adjusted under 35 U.S.C. 154(b) by 47 days.

(21) Appl. No.: 16/730,838

(22) Filed: Dec. 30, 2019

(65) Prior Publication Data
US 2021/0199598 A1 Jul. 1, 2021

(51) Int. Cl.
| | |
|---|---|
| G01R 27/04 | (2006.01) |
| G01N 22/00 | (2006.01) |
| G01N 22/04 | (2006.01) |
| G01N 21/3581 | (2014.01) |
| G01N 22/02 | (2006.01) |
| G01N 21/3563 | (2014.01) |
| G01N 27/02 | (2006.01) |
| A61B 5/05 | (2021.01) |
| A61B 5/0507 | (2021.01) |

(52) U.S. Cl.
CPC ......... *G01N 22/00* (2013.01); *G01N 21/3563* (2013.01); *G01N 21/3581* (2013.01); *G01N 22/02* (2013.01); *G01N 22/04* (2013.01); *G01N 27/02* (2013.01); *A61B 5/05* (2013.01); *A61B 5/0507* (2013.01)

(58) Field of Classification Search
CPC .... G01N 22/00; G01N 22/04; G01N 21/3581; G01N 22/02; G01N 21/3563; G01N 27/02; A61B 5/05; A61B 5/0507
USPC ... 324/76.11–76.83, 459, 600, 629, 637, 639
See application file for complete search history.

(56) References Cited

U.S. PATENT DOCUMENTS

| | | | |
|---|---|---|---|
| 2001/0033207 A1* | 10/2001 | Anderson | H01Q 9/26 333/99 PL |
| 2018/0136120 A1* | 5/2018 | Hammerschmidt | G01N 22/00 |
| 2018/0149536 A1* | 5/2018 | Choe | G11B 33/1486 |
| 2019/0084271 A1* | 3/2019 | Fruehling | B32B 7/04 |

(Continued)

*Primary Examiner* — Raul J Rios Russo
(74) *Attorney, Agent, or Firm* — Michael A. Davis, Jr.; Charles A. Brill; Frank D. Cimino

(57) ABSTRACT

A system includes first and second gas cells each comprising a respective sealed interior waveguide; first transmit antenna coupled to the first gas cell to provide a first electromagnetic wave to the first gas cell along a first direction; second transmit antenna coupled to the first gas cell to provide a second electromagnetic wave to the first gas cell along a second direction opposite the first direction; third transmit antenna coupled to the second gas cell to provide a third electromagnetic wave to the second gas cell; first receive antenna coupled to the first gas cell to generate a first signal indicative of an amount of energy in first electromagnetic wave; second receive antenna coupled to the second gas cell to generate a second signal indicative of an amount of energy in second electromagnetic wave; and processor to calculate a background-free signal based on a difference between first and second signals.

20 Claims, 11 Drawing Sheets

(56) References Cited

U.S. PATENT DOCUMENTS

2019/0346814 A1* 11/2019 Fruehling ................. G01S 7/35
2020/0272107 A1* 8/2020 Herbsommer ......... H03B 17/00

* cited by examiner

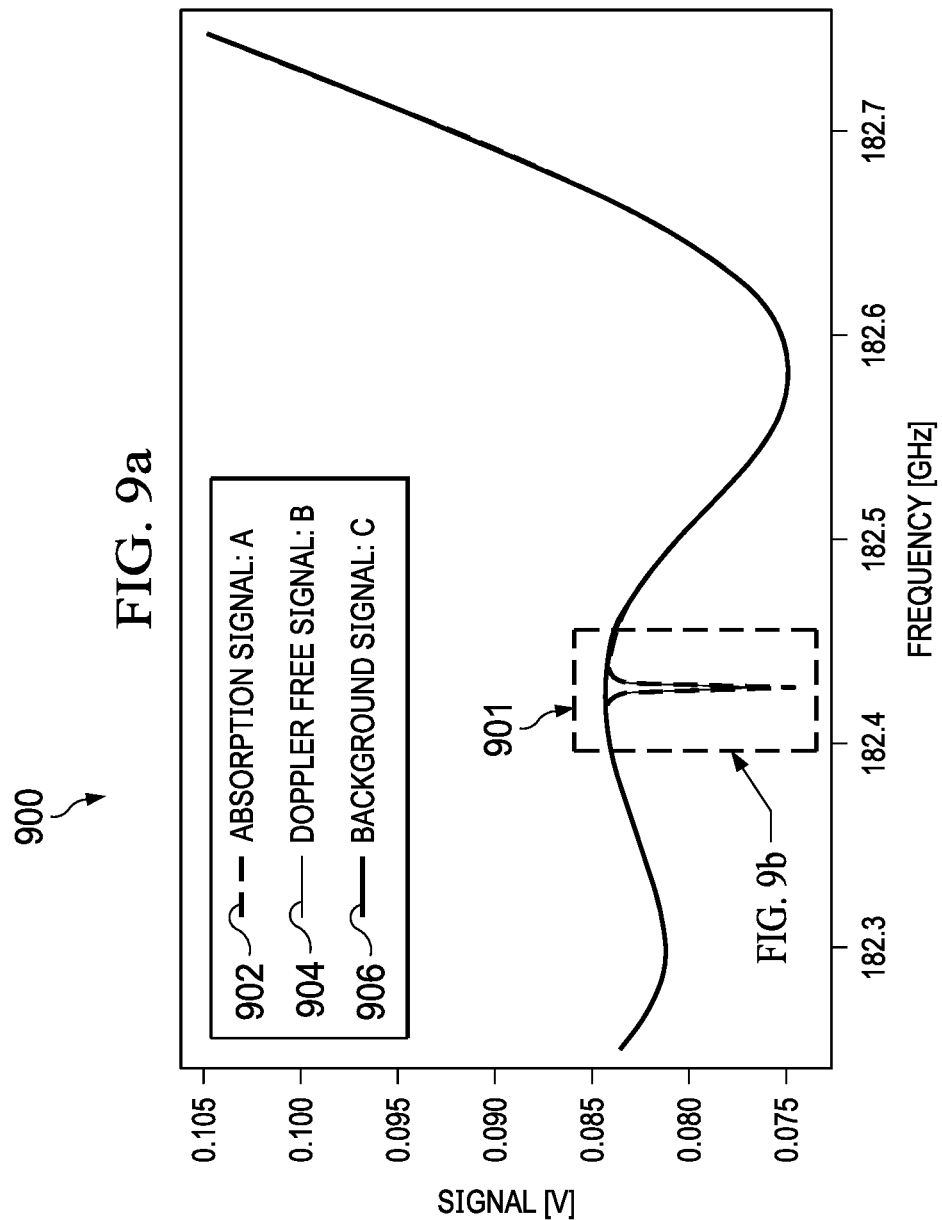

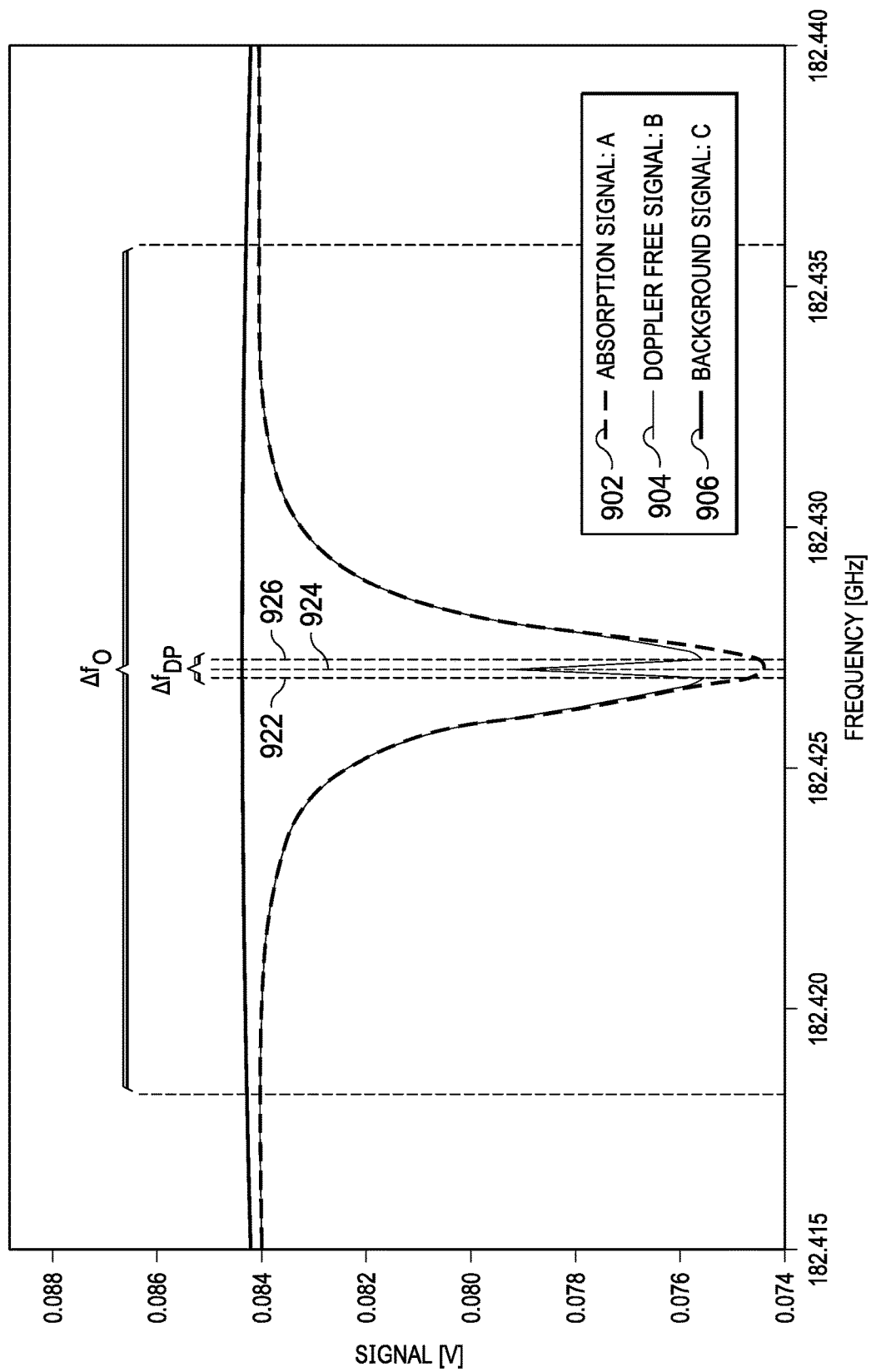

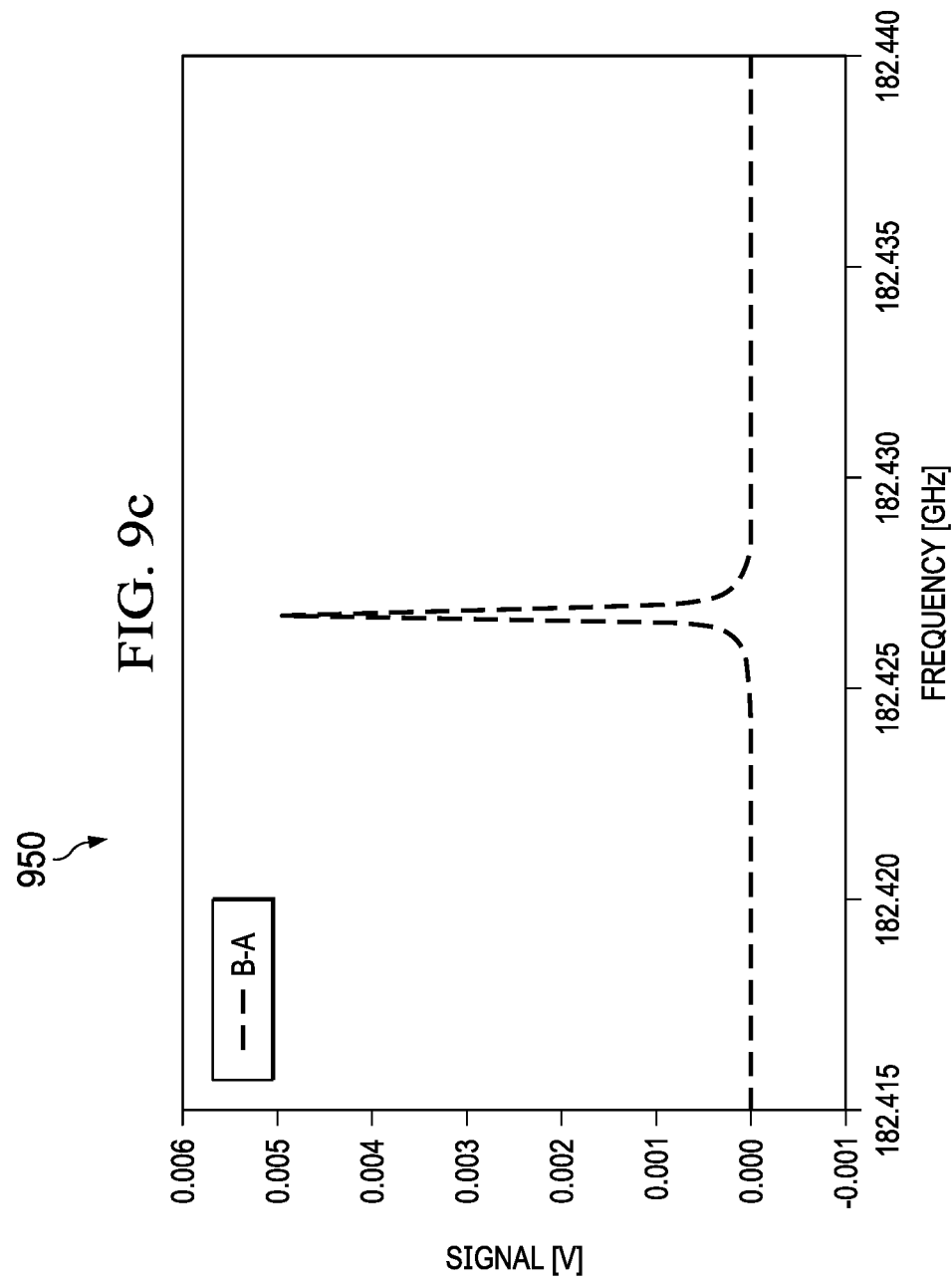

US 11,280,746 B2

BACKGROUND SUPPRESSION FOR DOPPLER-FREE MM-WAVE SPECTROSCOPY

BACKGROUND

This relates generally to spectroscopy, and more particularly to mm-wave spectroscopy.

SUMMARY

In at least one example, a system includes: first and second gas cells each including a respective sealed interior waveguide; a first transmit antenna coupled to the first gas cell and configured to provide a first electromagnetic wave to travel in the sealed interior of the first gas cell along a first direction; a second transmit antenna coupled to the first gas cell and configured to provide a second electromagnetic wave to travel in the sealed interior of the first gas cell along a second direction opposite the first direction; a third transmit antenna coupled to the second gas cell and configured to provide a third electromagnetic wave to travel in the sealed interior of the second gas cell; a first receive antenna coupled to the first gas cell and configured to generate a first signal indicative of an amount of energy in the first electromagnetic wave after travel through the first gas cell; a second receive antenna coupled to the second gas cell and configured to generate a second signal indicative of an amount of energy in the second electromagnetic wave after travel through the second gas cell; and a processor coupled to the first and second receive antennas and configured to calculate a background-free signal based on a difference between the first signal and the second signal.

In another example, a system includes: first and second gas cells each including a respective sealed interior waveguide; a first transmit antenna coupled to the first gas cell and configured to provide a first electromagnetic wave to travel in the sealed interior of the first gas cell along a first direction; a second transmit antenna coupled to the first gas cell and configured to provide a second electromagnetic wave to travel in the sealed interior of the first gas cell along a second direction opposite the first direction; a third transmit antenna coupled to the second gas cell and configured to provide a third electromagnetic wave to travel in the sealed interior of the second gas cell; and an electromagnetic coupler coupled to the gas cells. The electromagnetic coupler is configured to receive the first and third electromagnetic waves after travel through the first and second gas cells, and generate an electromagnetic wave indicative of a difference between the received first and second electromagnetic waves.

In yet another example, a method includes: providing a first electromagnetic wave to travel in a sealed interior waveguide of a first gas cell along a first direction; providing a second electromagnetic wave to travel in the sealed interior of the first gas cell along a second direction opposite the first direction; providing a third electromagnetic wave to travel in a sealed interior waveguide of a second gas cell; receiving the first and third electromagnetic waves after travel through the first and second gas cells; and generating a background-free signal based on a difference between the first and third electromagnetic waves.

BRIEF DESCRIPTION OF THE DRAWINGS

FIGS. 9a-9c show waveforms corresponding to energy absorption as a function of frequency for different gas cells or combinations thereof in accordance with various examples.

DETAILED DESCRIPTION

Figure 1:
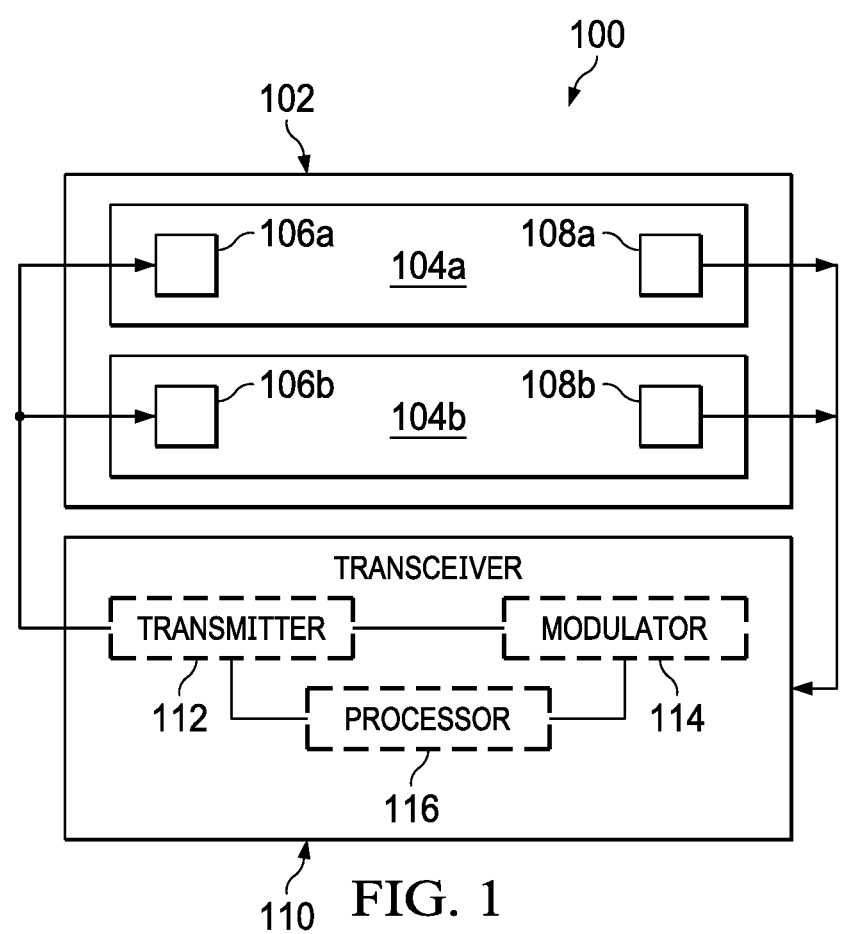
FIG. 1 shows a block diagram of a system for background suppression in accordance with various examples.

Stable clock signals, usable as a base frequency source either directly, or converted (e.g., divided down) to some multiple of a base frequency source, can be generated from various circuits and configurations. One example clock signal that demonstrates long-term stability is an atomic clock, which produces a signal in response to the natural and quantum response of atoms or molecules to an excitation source. In one example, such atoms are alkali metals stored in a chamber (e.g., a hermetic chamber), where the excitation source is one or more lasers directed to the cell and the response of the atoms in the chamber is detected by measuring the amount of laser energy (photons) that passes through the chamber as the laser frequency sweeps across a range. In another example, such molecules are dipolar gases also stored in a chamber, where the excitation source is an electromagnetic wave propagating through the chamber and the response of the molecules in the chamber is detected by measuring the amount of electromagnetic energy that passes through the chamber as the frequency of the source sweeps across a range. In the example where the excitation source is a laser, the wavelength of the electromagnetic field is on the order of 800 nm, which corresponds to approximately 1.5 eV of energy. However, in the example where the excitation source is a mm-wave source, the wavelength of the electromagnetic field is on the order of 2 mm, which corresponds to approximately 0.6 meV of energy.

An atomic clock apparatus may include a sealed chamber (e.g., a gas cell) that stores a dipolar gas. The gas cell includes an electromagnetic entrance into which an electromagnetic wave (or field) enters near a first end of the gas cell and an electromagnetic exit from which an electromagnetic wave exits near a second end of the gas cell. In another example, the electromagnetic wave enters and exits from the same port (e.g., after reflecting back from the opposite end of the gas cell). A transmitter may be coupled to the electromagnetic entrance to provide the electromagnetic wave to the gas cell, and a receiver may be coupled to the electromagnetic exit to receive the electromagnetic energy that passes through the gas cell. The electromagnetic wave that exits the gas cell is measured (e.g., by a diode detector) to determine an amount of absorption by (or transmission through) the dipolar gas, with the measure indicative of the quantum response of the gas as a function of the wave frequency. However, one or more of the transmitter, the receiver, the gas cell itself, and associated circuitry and electronic devices may add noise to or otherwise color the molecular absorption signal thus reducing the accuracy in determining the quantum response of the gas, and thus the accuracy and stability of the atomic clock.

Examples of this description address the foregoing by providing a similar electromagnetic wave to two gas cells, where one gas cell contains a dipolar gas, while the other gas cell does not contain a dipolar gas. For example, the gas cell not containing the dipolar gas may contain atmospheric gas, either at atmospheric pressure or at a pressure different than atmospheric pressure. In another example, the gas cell not containing the dipolar gas does not contain any gas (e.g., is approximately at vacuum). The response of the gas cell not containing the dipolar gas to electromagnetic wave interrogation is generally a background frequency response of the system (e.g., due to impacts on the frequency response observed by a receiver caused by transceiver circuitry, the gas cell itself, and other associated circuitry and electronic devices). However, the response of the gas cell containing the dipolar gas to electromagnetic wave interrogation also includes the quantum response of the gas as a function of the wave frequency. The gas cells are substantially similar in their physical characteristics, such as dimensions, shape, manufacturing processes, interior coatings, entry/exit passage construction, and the like, such that the response of the gas cell containing the dipolar gas also includes the background response in addition to the quantum response of the gas.

The response of the gas cell not containing the dipolar gas is subtracted from the response of the gas cell containing the dipolar gas, which effectively removes the background response and provides a background-free response. The background-free response can then be utilized by a transceiver to determine the quantum response of the gas with improved accuracy and stability, without being colored by the background frequency response of the various system components. As a result, the transceiver generates a precision clock signal with increased accuracy and stability.

FIG. 1 shows a block diagram of a system 100, which in one example is a clock system. The system 100 includes a semiconductor substrate 102 including a first gas cell 104a and a second gas cell 104b. The first and second gas cells 104a, 104b each include a passage 106a, 106b, respectively, which serves as an entrance into the gas cell 104a, 104b. The first and second gas cells 104a, 104b also each include a passage 108a, 108b, respectively, which serves as an exit from the gas cell 104a, 104b. A transceiver 110 is coupled to the gas cells 104a, 104b. In this example, the transceiver 110 includes a transmitter 112 (e.g., a sub-block of transceiver 110) that is configured to provide an electromagnetic wave to the gas cells 104a, 104b by way of their respective entry passages 106a, 106b. The transceiver 110 also includes a receiver 114 (e.g., a sub-block of transceiver 110) that is configured to receive the electromagnetic waves (or signals related thereto, such as an analog voltage signal) after travel through the gas cells 104a, 104b by way of their respective exit passages 108a, 108b. Although shown schematically as separate blocks for the purpose of describing their functionality, the transmitter 112 and/or the receiver 114 may share certain components (e.g., circuitry), at least some of which are described further below.

In this example, the transceiver 110 also includes a processor 116, although in other examples the processor 116 may be a distinct component relative to the transceiver 110. In this example, the transmitter 112, the receiver 114, and the processor 116 are coupled, while the processor 116 is configured to, among other things, control the transmitter 112 to provide electromagnetic waves to the gas cells 104a, 104b and process signals received from the gas cells 104a, 104b and provide such processed signals to the receiver 114. The transceiver 110 is configured to provide a stable reference clock signal in response to electromagnetic interrogation of the first and second gas cells 104a, 104b, which is described in further detail below. The electrical dipolar nature of dipolar gas provides a detectable response to an interrogating electromagnetic wave, as further described below.

In one example, the gas cells 104a, 104b are formed in connection with an integrated circuit wafer, which can include multiple layers affixed relative to the semiconductor substrate 102. In FIG. 1, as well as in various subsequent figures, the shape depicted of the gas cells 104a, 104b depicts a generally top-down view, such as a planar cross-sectional view parallel to the plane generally defined by the substrate 102 in which the gas storage cavities of gas cells 104a, 104b are formed. Generally, gas cells 104a, 104b include a sealed enclosure having an interior in which a gas is stored. More specifically, gas cells 104a, 104b are configured to store a dipolar gas, such as water vapor (H20), CH3CN, HC3N, OCS, HCN, NH3, and isotopes of these gases, or any other dipolar molecular gas, inside an enclosed cavity of the cell, the cavity being sealed by nature of shapes, layering, and the like relative to the semiconductor substrate 102 and layers that combine to enclose the dipolar gas at a relatively low (e.g., 0.1 mbar) pressure. In addition, in certain examples, one of the gas cells 104a, 104b does not contain a dipolar gas and may instead contain atmospheric gas. Further, in some examples, the gas cell 104a, 104b that does not contain the dipolar gas is not sealed and is instead left open to atmosphere. For reasons detailed below, the enclosed pressure of one or both of the gas cells 104a, 104b can be other than the example provided, as examples described herein afford additional beneficial results that are independent of, or minimally affected by, the sealed pressure of the dipolar gas.

In one example, the gas cells 104a, 104b also include, or are lined along most of their interior surfaces with, a material to facilitate the interior as a signal waveguide, where such material is, for example, a conductor or a dielectric. In an example, the cross-sectional shape of gas cells 104a, 104b is square, rectangular, trapezoidal, or other shapes, while the dimensions of gas cells 104a, 104b may vary, where the gas cells 104a, 104b are 30 to 150 mm long, 1 to 3 mm wide, and 0.5 to 1.5 mm tall, where selections of these or comparable sizes match properties for efficient wave propagation given the frequency of the desired wave. Further, while the longitudinal shape is linear in FIG. 1 (and other figures), it also may bend or turn so as to form, for example, a meandering path.

Figure 2:
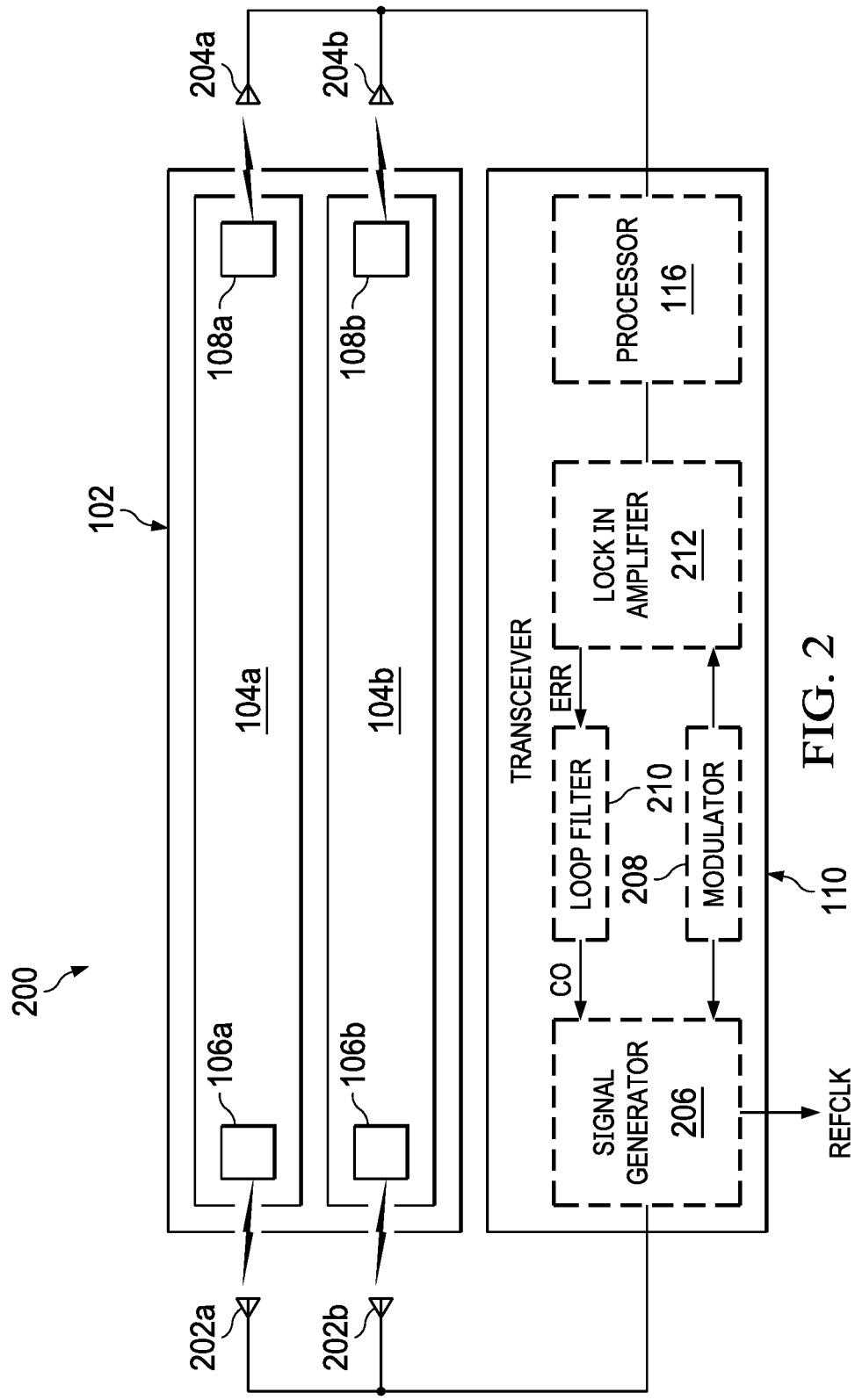
FIG. 2 shows another block diagram of a system for background suppression in accordance with various examples.

FIG. 2 shows a block diagram of a system 200, which is similar to the system 100 described above with regard to FIG. 1. However, in FIG. 2, the transceiver 110 is shown having functional sub-blocks including a signal generator 206, a modulator 208, a loop filter 210, and a lock-in amplifier 212, all of which are described in further detail below. These sub-blocks 206-212 support transmitter 112 and/or receiver 114 functionality. Additionally, the transceiver 110 is coupled to the entry passages 106a, 106b and configured to provide electromagnetic waves to the gas cells 104a, 104b by way of transmit antennas 202a, 202b, respectively. In an example, the transmit antennas 202a, 202b receive an analog voltage from the transceiver 110 and, in response to the received analog voltage, generate an electromagnetic wave that is provided to the gas cells 104a, 104b, respectively. The transceiver 110 is also coupled to the exit passages 108a, 108b and configured to receive the electromagnetic waves after travel through the gas cells 104a, 104b by way of receive antennas 204a, 204b, respectively. Although not shown schematically, in some examples the receive antennas 204a, 204b include a square-law detector or another type of detector that produce an output signal, for example, that is proportional to the intensity or amplitude of the received electromagnetic wave are coupled to the antennas 204a, 204b. Thus, in such examples, the receive antennas 204a, 204b receive an electromagnetic wave from the exit passages 108a, 108b and generate an analog voltage based on the received electromagnetic wave.

In the example of FIG. 2, the processor 116 processes the signals (e.g., analog voltages) generated by the receive antennas 204a, 204b before providing a resulting signal to the receiver 114 portion of the transceiver 110. However, as described further below, in other examples a different electromagnetic coupler resides intermediate to the exit passages 108a, 108b and the receive antennas 204a, 204b and generates a resulting electromagnetic wave based on the received electromagnetic waves from the exit passages 108a, 108b. Although shown schematically as separate components, it should be appreciated that in some examples the transceiver 110 (or separate transmitters and receivers, as the case may be) includes (e.g., as integrated devices) the associated antennas 202a, 202b, 204a, 204b (including square-law detectors as described above).

The transmit antennas 202a, 202b are positioned proximate the entry passages 106a, 106b, so that electromagnetic energy from the transceiver 110 may be communicated to the transmit antennas 202a, 202b and then into the gas cells 104a, 104b by way of entry passages 106a, 106b. As described in further detail below, in one example, a separate transmitter 112 or transceiver 110 (not shown in FIG. 2 for simplicity) provides the electromagnetic energy/wave to each of the gas cells 104a, 104b (e.g., by way of transmit antennas 202a, 202b). In another example, a single transmitter 112 or transceiver 110 provides the electromagnetic energy/wave, which is received by a directional coupler (not shown in FIG. 2 for simplicity) that generates first and second electromagnetic waves to be provided to the first and second gas cells 104a, 104b, respectively.

In the examples of FIGS. 1 and 2, the term passage in the context of the entry passages 106a, 106b and exit passages 108a, 108b suggests a signal communications pathway for passage of the electromagnetic signal, but not necessarily an open aperture to ambient per se that otherwise could cause the sealed dipolar gas in one or both of the gas cells 104a, 104b to escape. Such a pathway may be formed in various fashions, such as by a glass layer as the upper surface of the sealed enclosure of the gas cell and providing an opening in the metal surround that is otherwise formed within the cell—in this manner, an electromagnetic signal may pass through the opening and glass into the interior of the cell, thereby reaching the dipolar gas sealed therein. However, in other examples, the one of the gas cells 104a, 104b that does not contain a dipolar gas is not sealed and thus is open to atmosphere.

The transceiver 110 is both for transmitting (TX) and receiving (RX) signals. The transceiver 110 is generally described by way of example but not limitation, for accomplishing the transceiver and signal responsiveness described herein. In this regard, a signal generator 206 is connected, and is modulated by a modulator 208, to provide a base frequency controlled TX signal that, as detailed later, is swept across a particular frequency range from below to past the intrinsic quantum transition frequency for the dipolar gas in one of the gas cells 104a, 104b (e.g., 182.427 GHz for OCS). Modulator 208 modulates the frequency of the interrogation signal provided by the signal generator 206. The modulation frequency ranges, such as between 10 to 50 KHz.

After the signals pass through the gas cells 104a, 104b, they are received by the receive antennas 204a, 204b, respectively (or other electromagnetic coupler as described further below). As described above, the receive antennas 204a, 204b generate a signal in response to the received electromagnetic wave, such as an analog voltage. The processor 116 is coupled to the receive antennas 204a, 204b and receives the RX signal (e.g., analog voltage) from the receive antennas 204a, 204b. In some examples, the processor 116 converts the received analog RX signal to a digital value (e.g., using an integrated analog-to-digital (ADC) converter), while in other examples an external ADC resides intermediate to the receive antennas 204a, 204b and the processor 116 to provide the processor 116 with a digital RX signal.

A lock in amplifier 212 in turn receives a signal generated by the processor 116 (or other electromagnetic coupler). Particularly, receive antennas 204a, 204b are positioned proximate the exit passages 108a, 108b of the gas cells 104a, 104b, so that electromagnetic energy that travels through gas cells 104a, 104b may be communicated from the exit passages 108a, 108b to receive antennas 204a, 204b and then to transceiver 110 by way of the processor 116 and, more particularly, to lock in amplifier 212. Generally, lock in amplifier 212 uses the signal from the modulator 208 to measure the processed RX signal from the processor 116 (or other electromagnetic coupler) at the same modulation frequency provided by modulator 208. In this way, lock in amplifier 212 is able to reject noise outside the modulation frequency and thereby reduce the noise from the system.

As described in further detail below, in one example, a separate receive antenna 204a, 204b receives the electromagnetic energy/wave after travel through each of the gas cells 104a, 104b. The receive antennas 204a, 204b convert the electromagnetic wave into an RX signal, such as an analog voltage, which is further processed by the processor 116 before being utilized by the transceiver 110. In another example, an electromagnetic coupler (not shown in FIG. 2 for simplicity) receives and processes the electromagnetic energy/waves after travel through each of the gas cells 104a, 104b (e.g., in the electromagnetic domain), while one or more receive antennas receive the resultant processed electromagnetic wave from the electromagnetic coupler, convert the processed electromagnetic wave into an RX signal, such as an analog voltage, which is utilized by the transceiver 110. These examples are described further below.

In more detail, the TX signal may be a sinusoid, although other periodic oscillating signals also may be used, so long as such signal includes a Fourier component in the frequency of interest. The TX signal need not be continuous and thus in some examples is a discrete signal. The TX signal is provided to the gas cells 104a, 104b. Under feedback control, signal generator 206 also provides the reference clock REFCLK, which is refined using examples described herein. The RX signal (e.g., the analog voltage value received by the processor 116 in FIG. 2) represents an amount of the originally transmitted signal TX that passes through the gas cells 104a, 104b and contains the information of the absorption of the dipolar gas at the quantum rotations transition frequency. In examples of this description, the RX signal from each of the gas cells 104a, 104b (e.g., by way of receive antennas 204a, 204b and a square-law detector or similar device) is received by the processor 116, which generates a processed RX signal that is provided to the transceiver 110. In response to the processed RX signal, lock in amplifier 212 provides a signal that is the first derivative of the signal as it is swept in frequency. Consequently at the frequency corresponding to the quantum rotational molecular transition, the first derivative is zero and the error signal ERR is zero. At frequencies different from the quantum rotational transition, the signal ERR is not zero and provides a correction to the loop filter 210, allowing it to "lock" the clock to the quantum transition frequency. This apparatus also filters out noise as detected by reference to the modulation frequency provided by modulator 208. In one example, lock in amplifier 212 provides the error signal ERR as an in-phase output, and the error signal ERR is used as an input by a loop filter 210 (or controller circuit) for providing a control output signal CO to signal generator 206. As further detailed below, such feedback selectively adjusts the TX output signal frequency, following an initial sweep, to ultimately maintain this frequency at a peak absorption frequency of the dipolar molecular gas inside the sealed interior of the gas cell 104a, 104b that contains the dipolar gas, with that maintained frequency providing a stable output reference clock REFCLK. In some examples, the RF power of the TX and RX loop is controlled so as to avoid or mitigate stark shift effects (frequency shifts in response to quantum transition produced by the presence of an electric field).

As described above, one or more of the transmitter 112 and the receiver 114 (or transceiver 110), the gas cell 104 itself, and associated circuitry and electronic devices may add noise to or otherwise color the molecular absorption signal, thus reducing the accuracy in determining the quantum response of the gas, and thus the accuracy of the atomic clock as a precision clock source. Examples of this description address the foregoing providing a similar electromagnetic wave to two gas cells 104a, 104b, where one gas cell contains a dipolar (e.g., 104a), while the other gas cell does not contain a dipolar gas (e.g., 104b). The response of the gas cell not containing the dipolar gas 104b to electromagnetic wave interrogation is generally a background frequency response of the system 200 (e.g., due to impacts on the frequency response observed by a receiver caused by transceiver circuitry 202, the gas cell 104a, 104b itself, and other associated circuitry and electronic devices). However, the response of the gas cell containing the dipolar gas 104a to electromagnetic wave interrogation also includes the quantum response of the dipolar gas as a function of the wave frequency. The gas cells are substantially similar in their physical characteristics, such as dimensions, shape, manufacturing processes, interior coatings, entry/exit passage construction, and the like, such that the response of the gas cell containing the dipolar gas also includes the background response in addition to the quantum response of the gas.

In examples of this description, the response of the gas cell not containing the dipolar gas 104b is subtracted from the response of the gas cell containing the dipolar gas 104a (or vice versa), which effectively removes the background response and provides a background-free response, or a processed RX signal, which can then be utilized by the transceiver 110 (e.g., the lock in amplifier 212) to determine the quantum response of the gas with improved accuracy and stability, without being colored by the background frequency response of the various system components. As a result, the transceiver 110 generates the precision clock signal REFCLK with increased accuracy and stability. Various examples of this approach are described in further detail below.

Generally, the transceiver 110 is configured to sweep the modulated base frequency TX signal, such that the base frequency is swept across an initial frequency range that includes the intrinsic quantum rotational state transition frequency for the dipolar gas in the gas cell(s) 104a, 104b. Thus, in the example where the dipolar gas is OCS, the range will include the intrinsic quantum rotational state transition frequency of 182.427 GHz for OCS, and could include, for example, a sweep from approximately 182.25 GHz to 182.75 GHz.

In a first example, one of the gas cells 104a is filled with a dipolar gas, as described above, while the other of the gas cells 104b is not filled with a dipolar gas and may be filled with, for example, atmospheric gas. In another example, the gas cell 104b not containing the dipolar gas does not contain any gas (e.g., is approximately at vacuum). Since the gas cell 104b is not filled with a dipolar gas, the electromagnetic energy received from the exit passage 108b by the receiver 114 or transceiver 110 is indicative of a background signal absorption or transmission response of the system, which may include one or more of the transmitter 112 and the receiver 114 (or transceiver 110), the gas cell 104 itself, and associated circuitry and electronic devices such as the processor 116. A signal is generated (e.g., by the receive antennas 204a, 204b along with any intermediate device such as a square-law detector or similar device) that is indicative of the received electromagnetic energy.

Figure 3A:
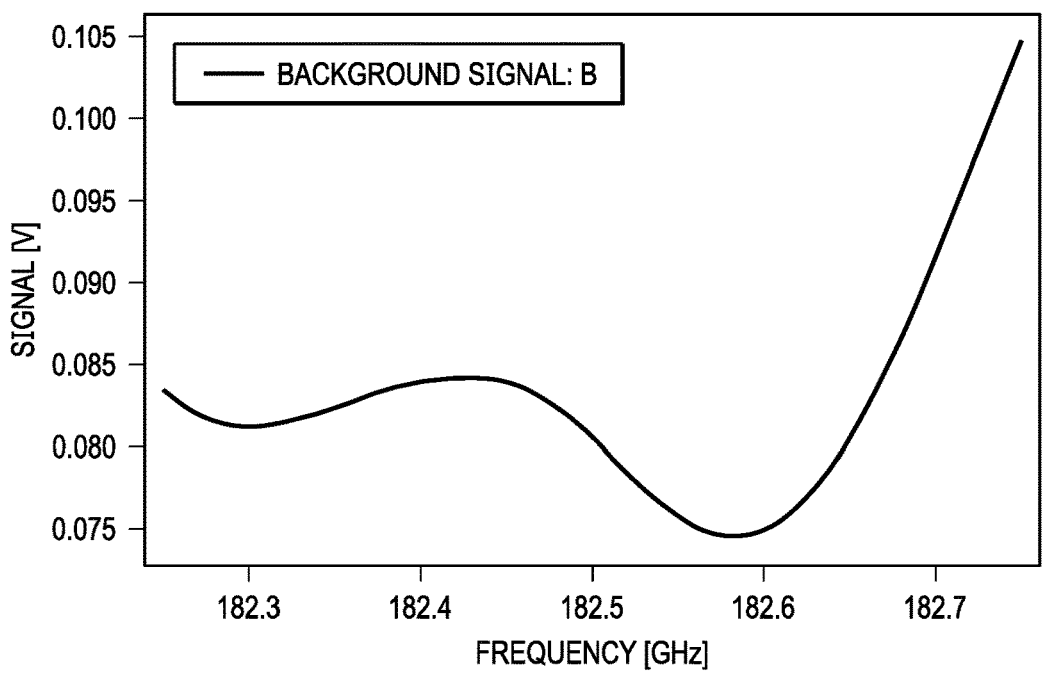
FIGS. 3a-3c show waveforms corresponding to energy absorption as a function of frequency for different gas cells or combinations thereof in accordance with various examples.

FIG. 3a shows a waveform 300 of an example background signal generated by the receive antennas 204a, 204b (e.g., by a square-law detector or similar device) in response to the electromagnetic energy received from the exit passage 108b of the gas cell 104b. For example, the waveform 300 shows transmission energy as a function of frequency of the received electromagnetic wave. Ideally, the background waveform 300 would be flat, which would indicate that the transmission (or absorption) of the system is independent of frequency. However, in real world examples, this is not the case.

Figure 3B:
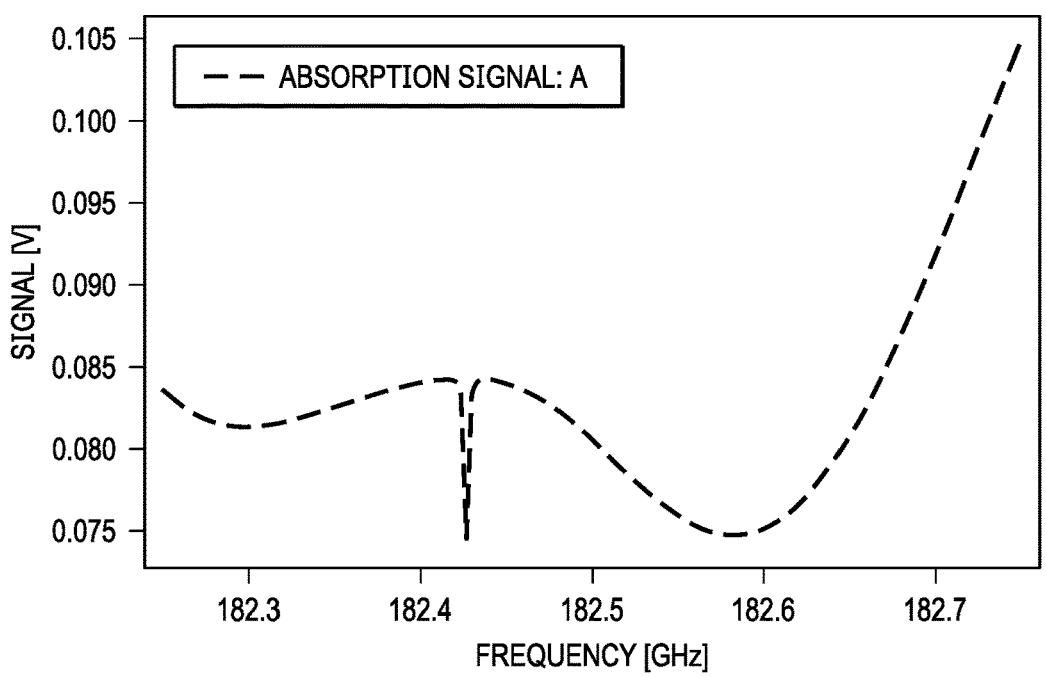

FIG. 3b shows a waveform 310 of an example RX energy transmission signal generated by the receive antenna 204a (e.g., by a square-law detector or similar device) in response to the electromagnetic energy received from the exit passage 108a of the gas cell 104a. For example, the waveform 400 shows the RX energy transmission through the dipolar gas in the gas cell 104a as a function of frequency of the received electromagnetic wave. In various examples, the gas cells 104a, 104b are substantially similar in their physical characteristics, such as dimensions, shape, manufacturing processes, interior coatings, entry/exit passage construction, and the like, such that the background response for the gas cells 104a, 104b is also substantially similar.

Figure 3C:
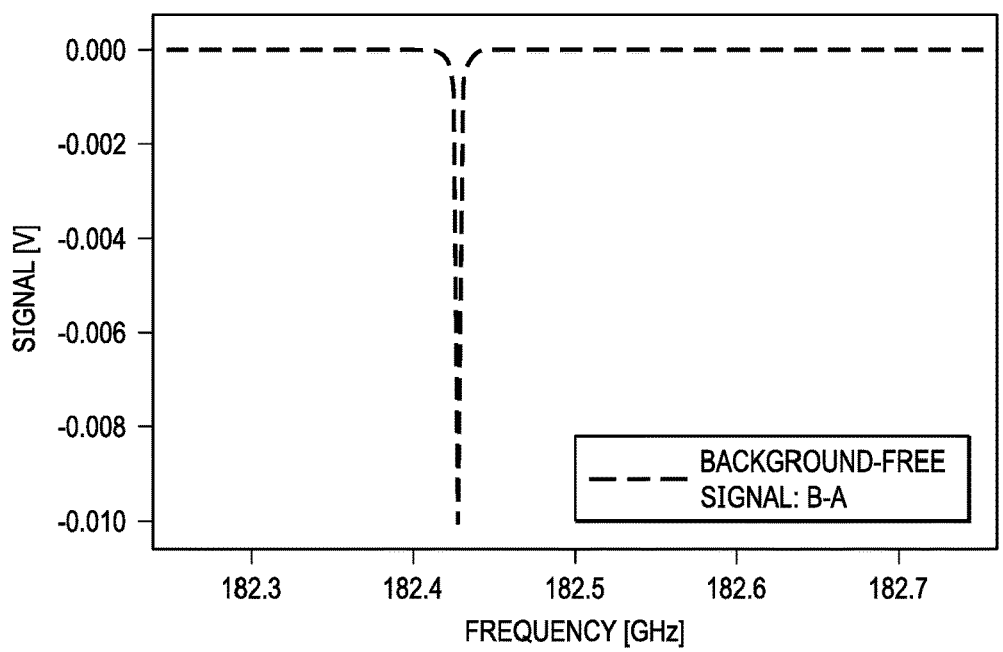

FIG. 3c shows a waveform 320 of an example background-free signal that results when the background waveform 300 (e.g., obtained from the receive antenna 204b coupled to the gas cell 104b that does not contain dipolar gas) is subtracted from the waveform 310 that reflects the RX energy transmission through the dipolar gas (e.g., obtained from the receive antenna 204a coupled to the gas cell 104a that contains dipolar gas). In another example, the waveform 310 that reflects the RX energy transmission through the dipolar gas is instead subtracted from the background waveform 300, which has the same effect but with a reversal in sign of values.

As described in further detail below, in some examples the processor 116 is configured to receive the background signal (e.g., waveform 300) and the gas transmission signal (e.g., waveform 310) and calculates the difference represented by the waveform 320. In other examples, an electromagnetic coupler is coupled to the exit passages 108a, 108b and thus receives the electromagnetic waves after travel through the gas cells 104a, 104b and generates a resulting electromagnetic wave that is indicative of the difference in the received waves. Thus, the background-free waveform 320 represents suppression of the impacts of gas cell 104 geometry, environment, or surrounding electronics like the transceiver 110, which increases the accuracy of determining the maximum absorption frequency and thus the accuracy and stability of the REFCLK signal that results from such determination.

Figure 4A:
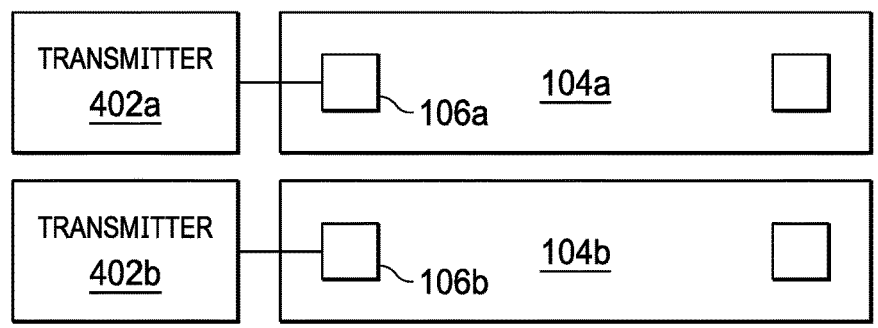
FIGS. 4a and 4b show various transmitter configurations in accordance with various examples.
Figure 4B:
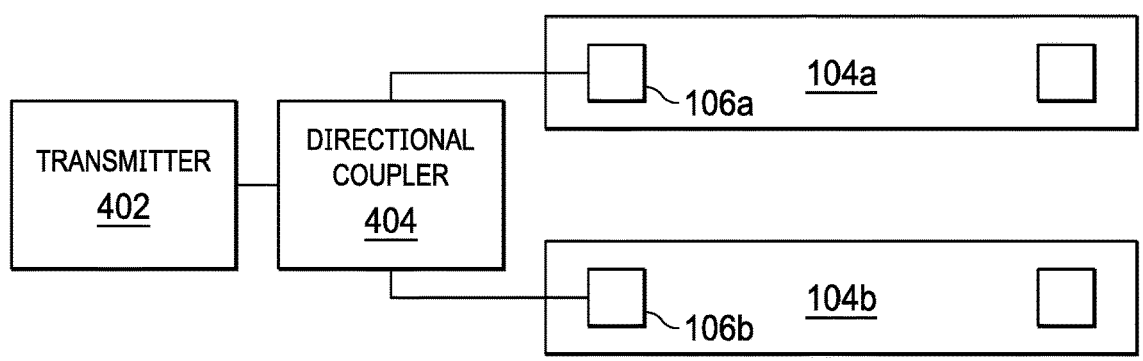

FIGS. 4a and 4b show examples of different transmitter configurations for providing electromagnetic waves to the entry passages 106a, 106b of the gas cells 104a, 104b. In the example of FIG. 4a, a first transmitter 402a (or a transmit portion of a first transceiver) is coupled to the entry passage 106a of the gas cell 104a (e.g., by first transmit antenna 202a, not shown for simplicity). Similarly, a second transmitter 402b (or a transmit portion of a second transceiver) is coupled to the entry passage 106b of the gas cell 104b (e.g., by second transmit antenna 202b, not shown for simplicity). In the example of FIG. 4a, the processor 116 (or other transmitter and/or transceiver circuitry) may be configured to cause the first and second transmitters 402a, 402b to provide approximately equal electromagnetic waves to the first and second gas cells 104a, 104b, respectively, such that the background response is approximately equal in the RX signals, facilitating elimination of the background response after the difference is calculated (e.g., by the processor 116 or other coupler, as described further below). In some examples, the electromagnetic waves provided to the first and second gas cells 104a, 104b have the same amplitude and the same frequency.

In the example of FIG. 4b, a single transmitter 402 (or a transmit portion of a single transceiver) is coupled to a directional coupler 404, which is in turn coupled to the entry passages 106a, 106b of the gas cells 104a, 104b (e.g., by way of first and second transmit antennas 202a, 202b, not shown for simplicity). The directional coupler 404 is configured to receive an electromagnetic wave from the transmitter 402 and generate corresponding electromagnetic waves, being approximately equal (e.g., by splitting the received electromagnetic wave energy), and providing those corresponding, split electromagnetic waves to the gas cells 104a, 104b. Similar to the example of FIG. 4a, since the corresponding electromagnetic waves are approximately equal, the background response is also approximately equal in the RX signals, facilitating elimination of the background response after the difference is calculated (e.g., by the processor 116 or other coupler, as described further below). In some examples, the electromagnetic waves provided to the first and second gas cells 104a, 104b have the same amplitude and the same frequency.

As described above, in some examples the processor 116 receives the background signal and the gas transmission signal from receive antennas 204a, 204b, which convert the received electromagnetic wave into, for example, an analog voltage. In such examples, the processor 116 determines a background-free signal based on the background and gas transmission signals. However, in other examples, an electromagnetic coupler receives the electromagnetic waves from the exit passages 108a, 108b and generates a resultant electromagnetic wave that is the result of subtracting the background signal from the gas transmission signal, or vice versa. This resultant electromagnetic wave is then converted to an analog voltage, which may optionally be processed (e.g., by the processor 116) and otherwise utilized by the transceiver 110 to generate the precision clock signal REFCLK as described above.

Figure 5A:
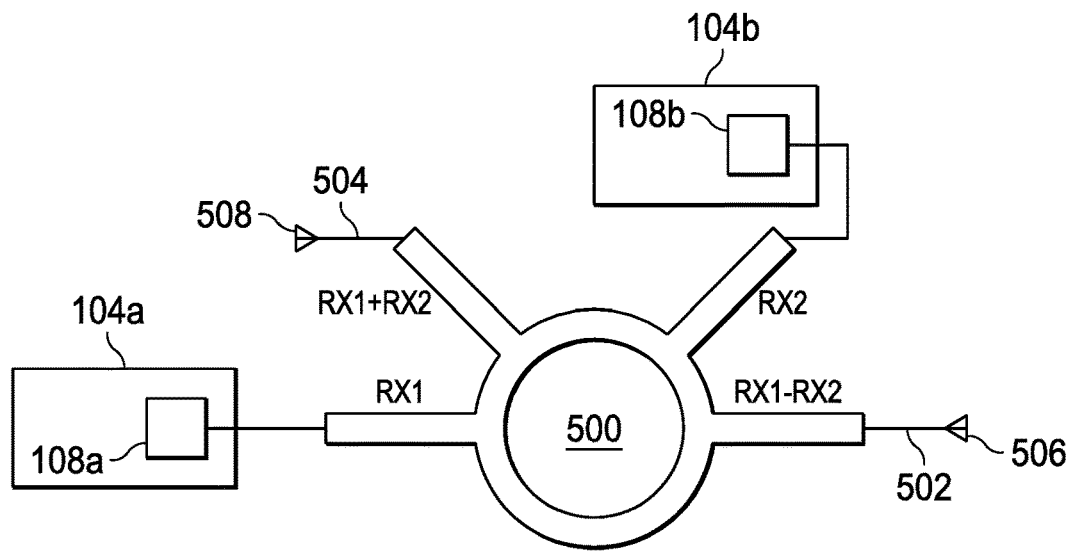
FIGS. 5a and 5b show various electromagnetic couplers in accordance with various examples.

FIG. 5a shows one example of an electromagnetic coupler, which is a rat-race coupler 500. The rate race coupler 500 is configured to receive electromagnetic waves from the exit passages 108a, 108b after travel through the gas cells 104a, 104b. The rat-race coupler 500 includes a first input RX1 coupled to the exit passage 108a of the gas cell 104a and a second input RX2 coupled to the exit passage 108b of the gas cell 104b. The rat-race coupler 500 also includes a first output 502 and a second output 504. In this example, the first output 502 produces an electromagnetic wave that corresponds to the difference of the first input RX1 and the second input RX2 (e.g., RX1−RX2), while the second output 804 produces an electromagnetic wave that corresponds to the sum of the first input RX1 and the second input RX2 (e.g., RX1+RX2).

The first output 502 is coupled to a receive antenna 506, while the second output 504 is coupled to a receive antenna 508. The receive antennas 506, 508 are functionally similar to the receive antennas 204a, 204b, described above, and thus are configured to produce an output signal, for example, that is proportional to the intensity or amplitude of the received electromagnetic wave. Thus, the receive antennas 506, 508 receive an electromagnetic wave from the outputs 502, 504, respectively, and generate an analog voltage based on the received electromagnetic wave.

Figure 5B:
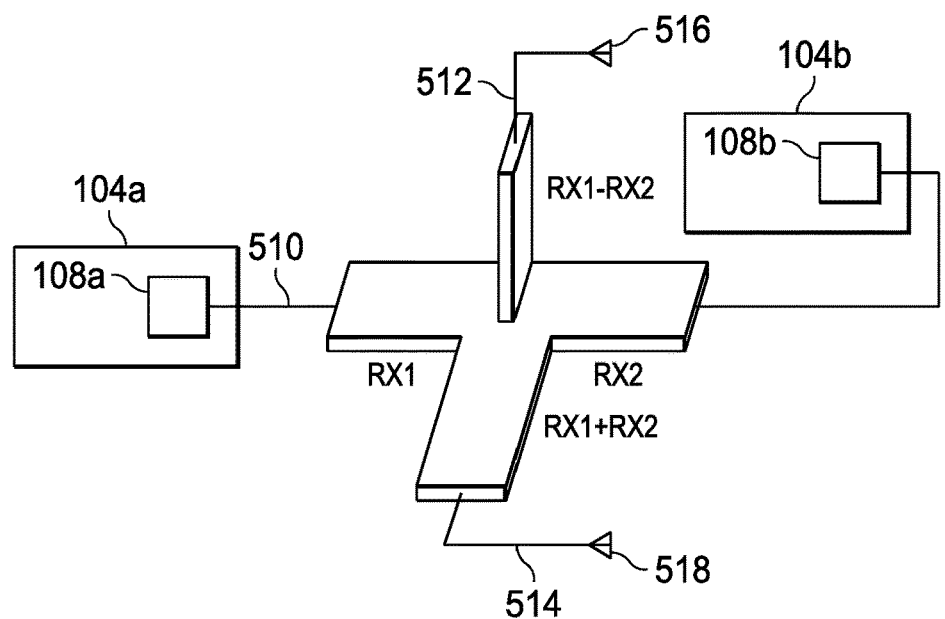

FIG. 5b shows another example of an electromagnetic coupler, which is a magic tee coupler 510. The magic tee coupler 510 is configured to receive electromagnetic waves from the exit passages 108b, 108b after travel through the gas cells 104a, 104b. The magic tee coupler 510 includes a first input RX1 coupled to the exit passage 108a of the gas cell 104a and a second input RX2 coupled to the exit passage 108b of the gas cell 104b. The magic tee coupler 810 also includes a first output 512 and a second output 514. In this example, the first output 512 produces an electromagnetic wave that corresponds to the difference of the first input RX1 and the second input RX2 (e.g., RX1−RX2), while the second output 514 produces an electromagnetic wave that corresponds to the sum of the first input RX1 and the second input RX1 (e.g., RX1+RX2).

The first output 512 is coupled to a receive antenna 516, while the second output 514 is coupled to a receive antenna 518. The receive antennas 516, 518 are functionally similar to the receive antennas 204a, 204b, described above, and thus are configured to produce an output signal, for example, that is proportional to the intensity or amplitude of the received electromagnetic wave. Thus, the receive antennas 516, 518 receive an electromagnetic wave from the outputs 512, 514, respectively, and generate an analog voltage based on the received electromagnetic wave.

Regardless of whether a rat-race coupler 500 or a magic tee coupler 510 is utilized, one of the outputs of the coupler 500, 510 corresponds to the difference between the electromagnetic waves after travel through the gas cells 104a, 104b. Thus, a single receive antenna may be utilized (e.g., with the output 502, 512 corresponding to the difference between the received electromagnetic waves), rather than the two receive antennas 204a, 204b shown above with respect to FIG. 2, in which the processor 116 calculates the background-free signal based on the difference in signals corresponding to the electromagnetic waves after travel through the gas cells 104a, 104b.

Figure 6A:
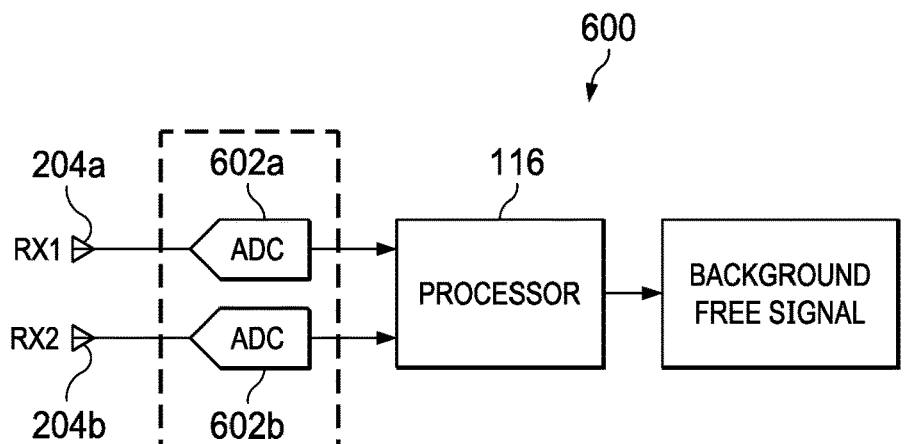
FIGS. 6a, 6b, and 6c show various receive antenna configurations in accordance with various examples.
Figure 6B:
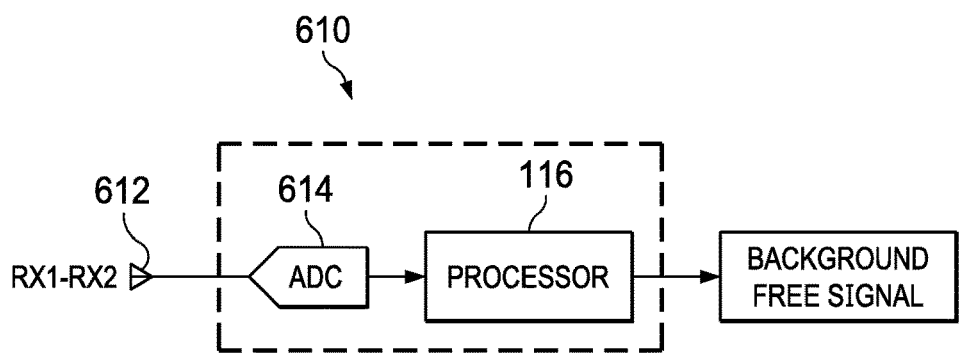
Figure 6C:
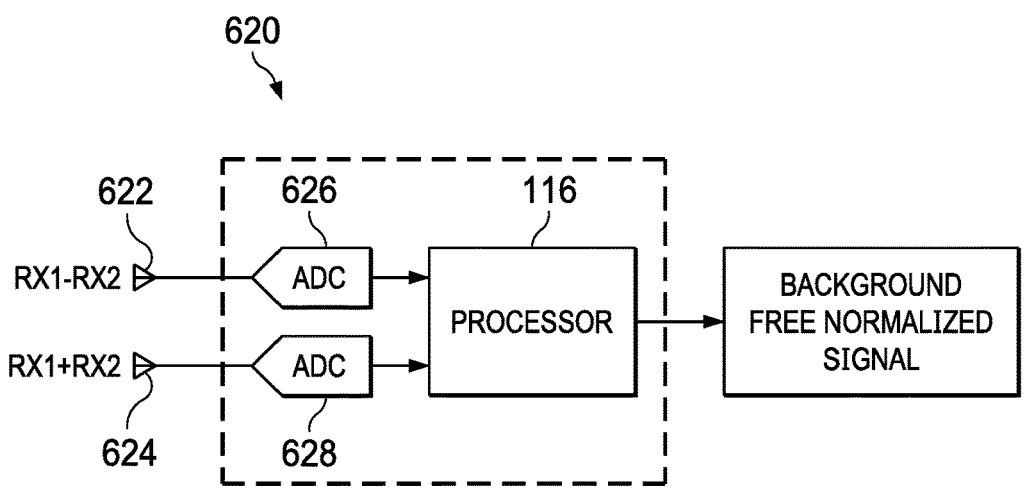

In certain examples of this description, various configurations of receive antennas are employed in conjunction with the processor 116 to determine a difference between the electromagnetic waves after travel through the gas cell 104a that contains the dipolar gas and the gas cell 104b that does not contain the dipolar gas. FIGS. 6a-6c show examples of such configurations. In FIG. 6a, the configuration shown corresponds to FIG. 2, described above. For example, the receive antenna configuration 600 of FIG. 6a includes receive antennas 204a, 204b, which receive electromagnetic waves from the exit passages 108a, 108b after travel through the gas cells 104a, 104b, respectively. In some examples, an ADC 602a, 602b is coupled to each receive antenna 204a, 204b, respectively, and receives the output signal from the receive antenna 204a, 204b and converts the output signal to a digital signal, which is then provided to the processor 116. In other examples, the processor 116 itself includes integrated ADCs that are coupled to the receive antennas 204a, 204b. In this example, since each output signal corresponds to the absorption or transmission characteristic of one of the gas cells 104a, 104b, the processor 116 is configured to calculate a background-free signal based on the difference between the received signals, such as described above with respect to FIGS. 3a-3c. In some examples, the processor 116 is further configured to calculate a normalized, background-free signal based on the difference between the received signals and a sum of the received signals. For example, a normalized, background-free signal may be given by:

$$(RX_1 - RX_2)/(RX_1 + RX_2)$$

The background-free signal (or normalized, background-free signal) is provided by the processor 116 to be utilized by the transceiver 110 to generate the precision clock signal REFCLK as described above.

FIG. 6b shows another example of a receive antenna configuration 610, which is utilized with an electromagnetic coupler such as those described above with respect to FIGS. 5a and 5b. In FIG. 6b, a single receive antenna 612 is coupled to the output of the electromagnetic coupler that corresponds to the difference of the input electromagnetic waves after travel through the gas cells 104a, 104b (e.g., RX1-RX2, or the output 506 of the rat-race coupler 500, or the output 516 of the magic tee coupler 510). The receive antenna 612 is functionally similar to the receive antennas 204a, 204b, described above. In one example, an ADC 614 is coupled to the receive antenna 612 and receives the output signal from the receive antenna 612 (e.g., an analog voltage) and converts the output signal to a digital signal, which is then provided to the processor 116. In this example, since the input to the receive antenna 612 already corresponds to the difference of the input electromagnetic waves after travel through the gas cells 104a, 104b, the processor 116 is configured to calculate a background-free signal based on the signal received from the receive antenna. The background-free signal is provided by the processor 116 to be utilized by the transceiver 110 to generate the precision clock signal REFCLK as described above. The processor 116 may additionally determine a maximum absorption frequency based on the background-free signal, which in turn enhances the accuracy and stability of the REFCLK signal that results from such determination.

FIG. 6c shows another example of a receive antenna configuration 620, which is utilized with an electromagnetic coupler such as those described above with respect to FIGS. 5a and 5b. In FIG. 6c, a receive antenna 622 is coupled to the output of the electromagnetic coupler that corresponds to the difference of the input electromagnetic waves after travel through the gas cells 104a, 104b (e.g., RX1-RX2, or the output 506 of the rat-race coupler 500, or the output 516 of the magic tee coupler 510). Additionally, a receive antenna 624 is coupled to the output of the electromagnetic coupler that corresponds to the sum of the input electromagnetic waves after travel through the gas cells 104a, 104b (e.g., RX1+RX2, or the output 508 of the rat-race coupler 500, or the output 518 of the magic tee coupler 510), which enables the example two-receiver system 620 to calculate a normalized, background-free signal. As described above, a normalized, background-free signal may be given by: $(RX_1 - RX_2)/(RX_1 + RX_2)$. The receive antennas 622, 624 are functionally similar to the receive antennas 204a, 204b, described above. In one example, an ADC 626, is coupled to the output of the receive antenna 622 and an ADC 628 is coupled to the output of the receive antenna 624 and receives the output signal from the receive antennas 622, 624 (e.g., an analog voltage) and converts the output signal to a digital signal, which is then provided to the processor 116. The processor 116 is configured to calculate the normalized, background-free signal based on the signals generated by the receive antennas 622, 624. The normalized, background-free signal is provided by the processor 116 to be utilized by the transceiver 110 to generate the precision clock signal REFCLK as described above. The processor 116 may additionally determine a maximum absorption frequency based on the normalized, background-free signal, which in turn enhances the accuracy and stability of the REFCLK signal that results from such determination.

Figure 7:
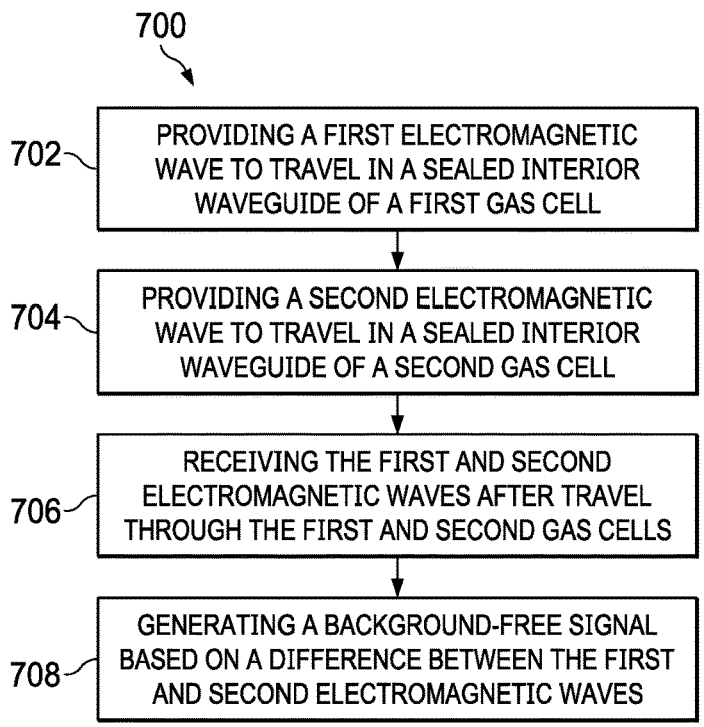
FIG. 7 shows a flow chart of a method for background suppression in accordance with various examples.

FIG. 7 shows a flow chart of a method 700 in accordance with examples of this description. The method 700 begins in block 702 with providing a first electromagnetic wave to travel in a sealed interior waveguide of a first gas cell. The method 700 then continues in block 704 with providing a second electromagnetic wave to travel in a sealed interior waveguide of a second gas cell. For example, as described above, an electromagnetic wave is provided to the gas cells 104a, 104b by transmit antennas 202a, 202b by way of entry passages 106a, 106b.

The method 700 continues further in block 706 with receiving the first and second electromagnetic waves after travel through the first and second gas cells. For example, after the signals pass through the gas cells 104a, 104b, they are received by the receive antennas 204a, 204b, respectively. As described above, the receive antennas 204a, 204b receive the electromagnetic waves and generate a signal in response to the received electromagnetic wave, such as an analog voltage. In another example, an electromagnetic coupler (e.g., a rat-race coupler 500 or a magic tee coupler 510 as described above with respect to FIGS. 5a and 5b) receives the electromagnetic wave after travel through the gas cells 104a, 104b and generates at least one output that is then received by a receive antenna.

As described above, one gas cell contains a dipolar gas (e.g., 104a), while the other gas cell does not contain a dipolar gas (e.g., 104b). The response of the gas cell not containing the dipolar gas 104b to electromagnetic wave interrogation is generally a background frequency response, while the response of the gas cell containing the dipolar gas 104a to electromagnetic wave interrogation also includes the quantum response of the dipolar gas as a function of the wave frequency. The differences in frequency response between the gas cells 104a, 104b may be leveraged to determine a background-free response. For example, the method 700 continues in block 708 with generating a background-free signal based on a difference between the first and second electromagnetic waves. In the example where receive antennas 204a, 204b receive the electromagnetic waves (and generate a signal in response), the processor 116 calculates the background-free signal based on the difference in signals corresponding to the electromagnetic waves after travel through the gas cells 104a, 104b. In examples where an electromagnetic coupler is utilized, one of the outputs of the coupler corresponds to the difference between the electromagnetic waves after travel through the gas cells 104a, 104b, and thus generates the background-free signal.

In addition to the foregoing, which improves the accuracy and stability of a precision clock source by reducing or eliminating the background response of the system from the analyzed quantum response of a dipolar gas, other examples additionally address Doppler broadening caused by molecules of dipolar gas having a velocity relative to the direction of electromagnetic wave propagation.

For example, the Allan deviation (which is the square root of the Allan variance) is a measure of frequency stability of clock signals (e.g., in clocks, oscillators, amplifiers), and in effect is a measure of frequency distribution over a number of samples. As a result, the lower the Allan deviation measure, the lower the variance of distribution and the better the performance of the clock signal. Further, the Allan deviation is inversely proportional to both the quality factor (Q) and signal-to-noise ratio (SNR) of the frequency response curve of the transceiver 110 in an example, as it processes the received RX signal response to detect an absorption peak frequency. By increasing one or both of the Q and SNR of the system, the Allan deviation measure is improved. Reducing the pressure in the gas cell 104a, 104b achieves certain improvements in the Allan deviation, as this pressure reduction reduces the width of the transition caused by pressure broadening phenomena. However, Q is only improved down to a certain pressure, while for pressures below a certain value (e.g., 0.1 mbar), the width cannot be reduced further because of Doppler broadening, which is independent of pressure and mostly dependent on the temperature of the gas. Pressure reduction also reduces the number of molecules available for interrogation and thus the amplitude of the quantum transition signal. An optimum pressure can be identified (for OCS this pressure is approximately 0.1 mbar) where the Allan deviation can be minimized by having the minimum transition width possible and the maximum amplitude possible.

As described above, existing systems can be susceptible to Doppler broadening, which is caused by the distribution of velocities of atoms/molecules, particularly in response to higher temperatures. Particularly, for atoms having velocities in a same direction as the direction of propagation of the electromagnetic wave, the Doppler effect will cause the transition of the dipolar molecules from the lower energy vibrational state to the higher energy vibrational state to occur when the frequency of the electromagnetic signal is lower than the frequency that corresponds to the energy difference of the two vibrational states (e.g., 182.427 GHz for OCS), and conversely, for atoms having velocities in an opposing direction as the prior art unidirectional signal, the Doppler effect will cause the rotational transition of those atoms to occur at an excitation frequency that is higher than the intrinsic quantum rotational state transition frequency for the dipole. Thus, the result of Doppler broadening is a wider spectral line when interrogating these atoms/molecules, which accordingly provides less accuracy in identifying a particular frequency of quantum transition.

Examples of this description address the foregoing by providing two gas cells containing a dipolar gas. One of the gas cells is coupled to two transmitters (or transmit antennas) to provide electromagnetic waves through the gas cell in opposite directions, while the other gas cell is coupled to one transmitter (or transmit antenna) to provide an electromagnetic wave through the gas cell in one direction. The response to electromagnetic wave interrogation of the gas cell that receives an electromagnetic wave in one direction is generally similar to the gas cell containing the dipolar gas described above, and includes the quantum response of the gas as a function of the wave frequency, containing a peak at the frequency where maximum absorption by the dipolar gas of the electromagnetic wave occurs. However, the response to electromagnetic wave interrogation of the gas cell that receives electromagnetic waves in opposite directions is a Doppler-free response, which is described in greater detail below. As described above, the gas cells are substantially similar in their physical characteristics, such as dimensions, shape, manufacturing processes, interior coatings, entry/exit passage construction, and the like, such that the response of each gas cell includes approximately the same background response in addition to the quantum response (both Doppler-induced and Doppler-free) of the gas.

The response of the gas cell that receives an electromagnetic wave in one direction is subtracted from the response of the gas cell that receives electromagnetic waves in opposite directions (or vice versa). As described further below, a processor or an electromagnetic coupler carries out such subtraction. As a result, the background and Doppler-induced responses are effectively removed, and a resulting signal is indicative of a background- and Doppler-free quantum response of the gas. The background- and Doppler-free quantum response is utilized by a transceiver to generate a precision clock signal (e.g., REFCLK) with improved accuracy and stability due to the Doppler-free nature of the response, and additionally without being colored by the background frequency response of the various system components.

Figure 8:
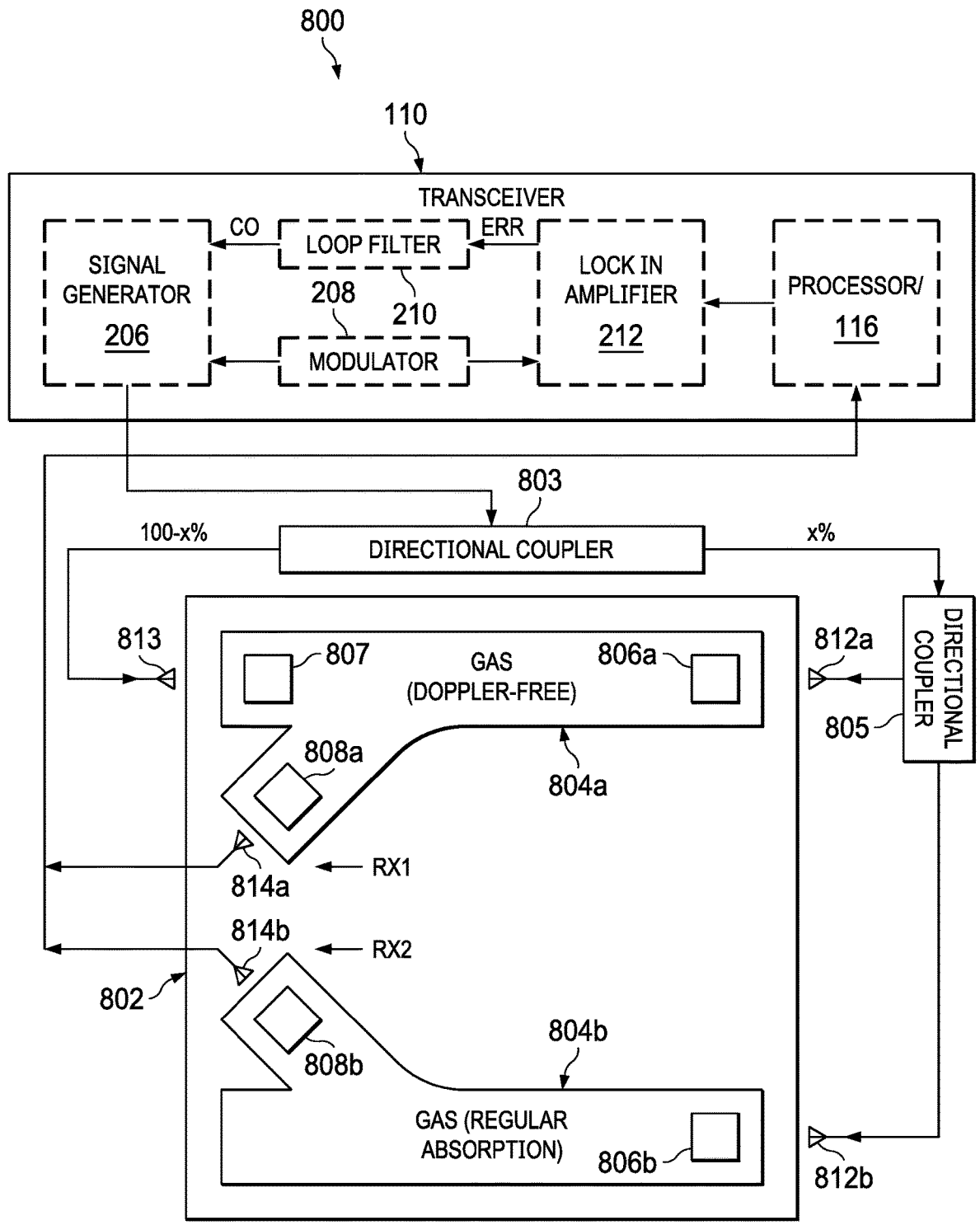
FIG. 8 shows a block diagram of a system for Doppler-free background suppression in accordance with various examples.

FIG. 8 shows a block diagram of a system 800, which in one example is a clock system. The system 800 includes a semiconductor substrate 802 including a first gas cell 804a and a second gas cell 804b. The first and second gas cells 804a, 804b each include a first passage 806a, 806b, respectively, which serves as an entrance into the gas cell 804a, 804b. The first gas cell 804a also includes a second passage 807 that serves as a second entrance into the gas cell 804a, so that electromagnetic waves may be provided to the gas cell 804a in opposite directions. The first and second gas cells 804a, 804b also each include a passage 808a, 808b, respectively, which serves as an exit from the gas cell 804a, 804b. In this example, the exit passages 808a, 808b are located in an additional cavity portion of the gas cells 804a, 804b that departs away from a linear portion of the gas cells 804a, 804b.

In one example, the gas cells 804a, 804b are formed in connection with an integrated circuit wafer, which can include multiple layers affixed relative to the semiconductor substrate 802. As described above, gas cells 804a, 804b include a sealed enclosure having an interior in which a dipolar gas is stored at a relatively low (e.g., 0.1 mbar) pressure.

In one example, the gas cells 804a, 804b also include, or are lined along most of their interior surfaces with, a material to facilitate the interior as a signal waveguide, where such material is, for example, a conductor or a dielectric. In an example, the cross-sectional shape of gas cells 104a, 104b is square, rectangular, trapezoidal, or other shapes, while the dimensions of gas cells 804a, 804b may vary, where the gas cells 804a, 804b are 30 to 150 mm long, 1 to 3 mm wide, and 0.5 to 1.5 mm tall, where selecting these or comparable sizes matches properties for efficient wave propagation given the frequency of the desired wave. Further, while the longitudinal shape is linear in FIG. 8 (and other figures), it also may bend or turn so as to form, for example, a meandering path.

A transceiver 110 (e.g., similar in function to the transceiver 110 described above with respect to FIGS. 1 and 2) is coupled to the gas cells 804a, 804b and is configured to provide an electromagnetic wave to a directional coupler 803, which receives the electromagnetic wave and divides the power of the received electromagnetic wave into two electromagnetic waves as outputs. The directional coupler 803 provides one of its outputs to a transmit pump antenna 813 and the other of its outputs to a second directional coupler 805. The second directional coupler 805 is similar in function to the directional coupler 803, and provides one of its outputs to transmit probe antenna 812a and the other of its outputs to transmit probe antenna 812b. In an example, the power provided to the transmit pump antenna 813 is greater than the power provided to the transmit probe antennas 812a, 812b, while the power provided to the transmit probe antennas 812a, 812b is approximately equal. For example, the directional coupler 803 provides 90% of the received electromagnetic wave power to the transmit pump antenna 813 and the remaining 10% of the received electromagnetic wave power to the directional coupler 805. The directional coupler 805 then provides approximately 50% of the received electromagnetic wave power (or 5% of the power provided to the directional coupler 803) to each of the transmit probe antennas 812a, 812b.

The transceiver 110 is coupled through the directional couplers 803, 805 to the gas cells 804a, 804b by way of their respective entry passages 806a, 806b, 807. The transceiver 110 is also coupled to the gas cells 804a, 804b and is configured to receive the electromagnetic waves after travel through the gas cells 804a, 804b by way of their respective exit passages 808a, 808b.

For example, the transmit probe antennas 812a, 812b are positioned proximate the entry passages 806a, 806b, so that electromagnetic energy from the transceiver 110, through directional couplers 803, 805, may be communicated to the transmit probe antennas 812a, 812b and then into the gas cells 804a, 804b by way of entry passages 806a, 806b. Additionally, the transmit pump antenna 813 is positioned proximate the entry passage 807, so that electromagnetic energy from the transceiver 110, through directional coupler 803, maybe communicated to the transmit pump antenna 813 and then into the gas cell 804a, in a direction opposite the electromagnetic energy provided by the transmit probe antenna 806a. As described in further detail below, in one example, a separate transmitter or transceiver 110 (not shown in FIG. 8 for simplicity) provides the electromagnetic energy/wave to each of the gas cells 804a, 804b (e.g., by way of transmit probe antennas 812a, 812b and transmit pump antenna 813). In another example, a single transmitter or transceiver 110 provides the electromagnetic energy/wave, which is divided by the directional couplers 803, 805 as described above.

The transceiver 110 is similar to the transceiver 110 described above, and is both for transmitting (TX) and receiving (RX) signals. The transceiver 110 generally provides a controlled TX signal that is swept across a particular frequency range from below to past the intrinsic quantum rotational state transition frequency for the dipolar gas in the gas cells 804a, 804b (e.g., 182.427 GHz for OCS). After the signal passes through the gas cell, it is received by the transceiver 110 coupled to receive the RX signal from receive antennas 814a, 814b. Particularly, receive antennas 814a, 814b are positioned proximate the exit passages 808a, 808b of the gas cells 804a, 804b, so that electromagnetic energy that travels through gas cells 804a, 804b may be communicated from the exit passages 808a, 808b to receive antennas 814a, 814b and then to transceiver 110. Although not shown schematically, in some examples the receive antennas 804a, 804b include a square-law detector or another type of detector that produce an output signal, for example, that is proportional to the intensity or amplitude of the received electromagnetic wave are coupled to the antennas 804a, 804b. Thus, in such examples, the receive antennas 804a, 804b receive an electromagnetic wave from the exit passages 808a, 808b and generate an analog voltage based on the received electromagnetic wave. Further, although shown schematically as separate components, it should be appreciated that in some examples the transceiver 110 (or separate transmitters and receivers, as the case may be) includes (e.g., as integrated devices) the associated antennas 812a, 812b, 813, 814a, 814b (including square-law detectors as described above).

Similar to above in FIGS. 5a, 5b, and 6a-6c, in one example, a separate receive antenna 814a, 814b receives the electromagnetic energy/wave after travel through each of the gas cells 804a, 804b. The receive antennas 814a, 814b convert the electromagnetic wave into an RX signal, such as an analog voltage, which is further processed by the processor 116 before being utilized by the transceiver 110. In another example, an electromagnetic coupler similar to those shown in FIGS. 5a and 5b receives and processes the electromagnetic energy/waves after travel through each of the gas cells 804a, 804b (e.g., in the electromagnetic domain), while one or more receive antennas receive the resultant processed electromagnetic wave from the electromagnetic coupler, convert the processed electromagnetic wave into an RX signal, such as an analog voltage, which is utilized by the transceiver 110.

As described above, a processor 116 is coupled to the transceiver 110 and is configured to, among other things, control the transceiver 110 to provide electromagnetic waves to the gas cells 804a, 804b and process signals received from the gas cells 804a, 804b and provide such processed signals to the transceiver 110. The transceiver 110 is configured to provide a stable reference clock signal in response to electromagnetic interrogation of the gas cells 804a, 804b, which is described in further detail below.

As described above, one or more of the transceiver 110, the gas cells 804a, 804b, and associated circuitry and electronic devices such as the processor 116 may add to or color the frequency response observed at the transceiver 110 and processed by the processor 116, which affects the accuracy of the determined quantum response of the gas, and thus the accuracy of the atomic clock as a precision clock source. Additionally, Doppler broadening results in a wider spectral line when interrogating the dipolar gas (or other atoms/molecules), which accordingly provides less accuracy in identifying a particular frequency of the quantum transition, further affecting the accuracy and stability of the atomic clock as a precision clock source. Examples of this description address the foregoing by subtracting the response of the gas cell 804b that receives an electromagnetic wave in one direction from the response of the gas cell 804a that receives electromagnetic waves in opposite directions (or vice versa). As a result, the background and Doppler-induced responses are effectively removed, and a resulting signal is indicative of a background- and Doppler-free quantum response of the gas. The background- and Doppler-free quantum response is utilized by the transceiver 110 to generate the precision clock signal REFCLK with improved accuracy and stability due to the Doppler-free nature of the response, and additionally without being colored by the background frequency response of the various system components. Various examples of this approach are described in further detail below.

Generally, the following refers to feedback control between the processor 116 and the transceiver 110. However, in certain examples, the transceiver 110 may provide feedback control independently of the processor 116. For example, the transceiver 110 sweeps the modulated base frequency TX signal such that the base frequency is swept across an initial frequency range that includes the intrinsic quantum rotational state transition frequency for the dipolar gas in gas cells 804a, 804b. Thus, in the example where the dipolar gas is OCS, the range will include the intrinsic quantum rotational state transition frequency of 182.427 GHz for OCS, and could include, for example, a sweep from 182.25 GHz to 182.75 GHz. Thus, the TX signal delivers an energy E to directional coupler 803, sweeping across this frequency range, so that the same frequency is simultaneously applied by both the transmit pump antenna 813 and the transmit probe antennas 812a, 812b. As a result, bidirectional propagation in opposite directions is accomplished for the gas cell 804a, while unidirectional propagation in one direction is accomplished for the gas cell 804b. In one example, while the TX signal represents a certain amount of energy E, the directional coupler 803 couples a first amount E1 of that energy to the directional coupler 805 and a second amount E2 of that energy (e.g., subject to possible signal loss TX−E1=E2) to the transmit pump antenna 813. Preferably E2>E1, where for example E2 may be 90% of TX, leaving 10% of TX as E1. The directional coupler 805 provides approximately equal energy (e.g., 0.5*E1) to each of the transmit probe antennas 812a, 812b.

The different transmitter examples described above with respect to FIG. 4a also apply to the example of FIG. 8, in which a background- and Doppler-free quantum response of gas is determined. For example, a first, second, and third transmitter (or transmit portions of first, second, and third transceivers) are coupled to the entry passages 806a, 807, 806b, respectively (e.g., by transmit antennas 812a, 813, 812b, respectively). In this example, the processor 116 (or other transmitter and/or transceiver circuitry) may be configured to cause the first and third transmitters to generate approximately equal electromagnetic waves to the first and second gas cells 804a, 804b, respectively, and to cause the second transmitter to generate an electromagnetic wave to the first gas cell 804a in direction opposite the first transmitter. In an example, the second transmitter generates an electromagnetic wave having a greater amount of energy than those generated by the first and third transmitters.

FIG. 9a shows a set of waveforms 900 of example signals generated by a receiver or the transceiver 110 in response to the electromagnetic energy received from the exit passages 808a, 808b of the gas cells 804a, 804b. For example, the waveform 902 shows transmission energy as a function of frequency of the received electromagnetic wave from the gas cell 804b, which is Doppler-broadened as described above, due to the unidirectional propagation of the electromagnetic wave in the gas cell 804b. The waveform 904 shows transmission energy as a function of frequency of the received electromagnetic wave from the gas cell 804a, which is Doppler-free due to the bidirectional propagation of the electromagnetic waves in the gas cell 804a, which is described in further detail below. The waveform 906 shows an example background signal, similar to that described above with respect to the systems of FIGS. 1 and 2, which is present in both the waveform 902 and 904, and thus is superimposed on those portions of the waveforms 902 and 904 that demonstrate the background response.

FIG. 9b shows a portion 901 of FIG. 9a in zoomed in detail, and also includes the Doppler-broadened signal waveform 902 (from gas cell 804b), the Doppler-free waveform 904 (from gas cell 804a), and the background signal waveform 906. The Doppler-broadened signal waveform 902 is similar to the absorption waveform described above with respect to FIG. 4 and, indeed, the gas cell 804b is generally similar in function to the gas cell 104b with exception for particular geometric differences. However, the bidirectional propagation of electromagnetic waves in opposite directions in the gas cell 804a results in a Doppler-free signal received by the receive antenna 814a from the exit passage 808a.

The transmit probe antenna 812a and transmit pump antenna 813 transmit at the same frequency, and that frequency is swept across a range that includes the intrinsic quantum rotational state transition frequency for the dipole (e.g., 182.427 GHz for OCS). Generally, therefore, the sweeping of frequency may be low to high (or high to low), producing the response shape depicted in FIG. 9b as waveform 904. Note that while FIGS. 9a and 9b plot transmission, absorption could be equivalently analyzed. In any event, as the swept frequency approaches the intrinsic quantum rotational state transition frequency, the transmission of energy through the dipolar gas decreases as shown, and as detected in the RX signal, creates an absorption spectra that is flatter away from that intrinsic frequency and that ascends from both directions as the frequency sweep nears the dipolar gas intrinsic frequency. Additionally, as the intrinsic frequency is approached, a first peak 922 occurs which is shown as a minimum in terms of energy transmission and at a frequency below the Doppler free frequency 924, and similarly above the Doppler free frequency 924 a second peak 926 occurs. As further detailed below, however, example embodiments are able to detect an additional peak as the Doppler free frequency 924, between peaks 922 and 926.

Regarding the Doppler-free response of the gas cell 804a, in an example one of the bidirectional TX signals is provided at a higher energy than the other by virtue of the directional coupler 803, where for sake of convention in other technologies the higher-energized signal is termed the pump. As a result, most of the atoms/molecules interrogated by the higher-energized signal from the transmit pump antenna 813, at the appropriate quantum frequency, will be excited to an energy level higher than a lower energy (e.g., ground) state, while other of the atoms/molecules will remain at the lower energy state. Thus in response to the signal from the transmit probe antenna 812a, the number of molecules that are in the ground state is significantly reduced because most of them have been excited to the excited state by the transmit pump antenna 813 signal causing a decrease in the absorption profile, or an increase in the transmission profile.

In addition, the bidirectional or counter-propagating nature of the probe (813) and pump (812a) signals also reduces or eliminates the Doppler effect. Particularly, atoms/molecules at zero velocity do not demonstrate or experience the Doppler effect, and are accordingly affected by the frequency aspect of both of the counter-propagating waves, where again the pump (813) signal has depopulated a portion of the ground state to the higher energy state. As a result of the preceding, fewer of the ground state atoms remain at the Doppler-free frequency 924, so there are fewer atoms to absorb the probe (812a) energy and a corresponding drop in absorption, where such lack of absorption of that probe (812a) energy is evident in the resultant RX plot of FIG. 9b, which includes an increase in transmission energy centered around the intrinsic frequency 924, the increase in transmission arising from the fewer low-energy atoms to absorb the probe (812a) signal, which is the signal received by the receive antenna 814a. Thus, the gas cell 804a provides so-called Doppler-free spectroscopy, in that Doppler broadening is no longer an issue under this approach. In some examples, the Doppler-free benefits may be realized independently of the gas pressure in the gas cell 804a.

Further, the frequency width between peaks 922 and 926, DP is less than the frequency width ΔfO of the outer Gaussian descending portions of the plot. As a result, the Q relative to the frequency width ΔfDP is considerably better than the Q relative to the frequency width ΔfO of the outer descending portions. Accordingly, the improved Q of the Doppler free architecture improves the Allan deviation of system 800 (and the other comparable systems described herein).

FIG. 9c shows a waveform 950 of an example Doppler-free, background-free signal that results when the Doppler-broadened waveform 902 (e.g., obtained from the receive antenna 814b coupled to the gas cell 804b that experiences only unidirectional propagation of the electromagnetic wave) is subtracted from the Doppler-free waveform 904 (e.g., obtained from the receive antenna 814a coupled to the gas cell 804a that experiences bidirectional propagation of electromagnetic waves in opposite directions as described above). As described in further detail below, in some examples the processor 116 is configured to receive the Doppler-broadened signal (e.g., waveform 902) and the Doppler-free signal (e.g., waveform 904) and calculates the difference represented by the waveform 950. In other examples, as described above with respect to FIGS. 5a, 5b, 6b, and 6c, an electromagnetic coupler is utilized that receives the electromagnetic waves after travel through the gas cells 804a, 804b and generates a resulting electromagnetic wave that is indicative of the difference in the received waves. Thus, the Doppler-free and background-free waveform 950 represents suppression of the impacts of gas cell 804 geometry, environment, or surrounding electronics like the transmitter or transceiver 110, in addition to the Doppler broadening effect described above, which increases the accuracy of determining the maximum absorption frequency and thus the accuracy and stability of the REFCLK signal that results from such determination.

Figure 10:
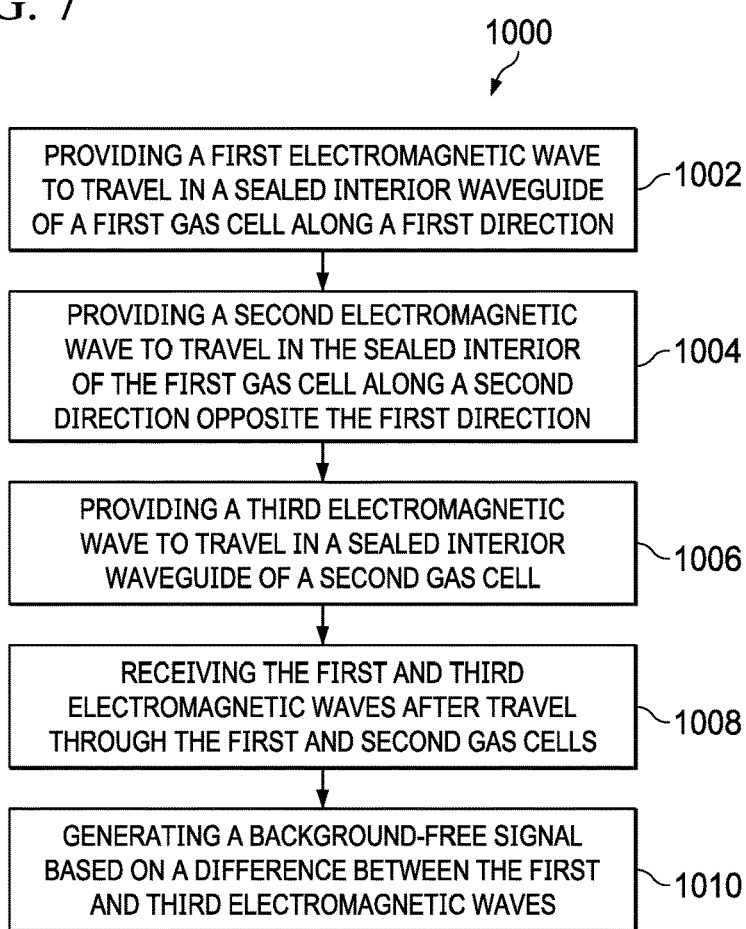
FIG. 10 shows a flow chart of a method for Doppler-free background suppression in accordance with various examples.

FIG. 10 shows a flow chart of another method 1000 in accordance with examples of this description. The method 1000 begins in block 1002 with providing a first electromagnetic wave to travel in a sealed interior waveguide of a first gas cell along a first direction. The method 1000 continues in block 1004 with providing a second electromagnetic wave to travel in the sealed interior of the first gas cell along a second direction opposite the first direction. For example, as described above, an electromagnetic wave is provided to the gas cell 804a by the transmit probe antenna 812a positioned proximate the entry passage 806a. Additionally, an electromagnetic wave is provided to the gas cell 804a by the transmit pump antenna 813 positioned proximate the entry passage 807. Thus, electromagnetic energy is communicated to the transmit pump antenna 813 and then into the gas cell 804a, in a direction opposite the electromagnetic energy provided by the transmit probe antenna 806a. The method 1000 continues in block 1006 with providing a third electromagnetic wave to travel in a sealed interior waveguide of a second gas cell. For example, as described above, an electromagnetic wave is provided to the gas cell 804b by the transmit probe antenna 812b positioned proximate the entry passage 806b.

The method 1000 continues further in block 1008 with receiving the first and third electromagnetic waves after travel through the first and second gas cells. For example, after the signals from the transit probe antennas 806a, 806b pass through the gas cells 804a, 804b, they are received by the receive antennas 808a, 808b, respectively. As described above, the receive antennas 808a, 808b receive the electromagnetic waves and generate a signal in response to the received electromagnetic wave, such as an analog voltage. In another example, an electromagnetic coupler (e.g., a rat-race coupler 500 or a magic tee coupler 510 as described above with respect to FIGS. 5a and 5b) receives the electromagnetic wave from the transit probe antennas 806a, 806b after travel through the gas cells 804a, 804b and generates at least one output that is then received by a receive antenna.

Finally, the method 1000 continues in block 1010 with generating a background-free signal based on a difference between the first and third electromagnetic waves. As described above, one or more of the transceiver 110, the gas cells 804a, 804b, and associated circuitry and electronic devices such as the processor 116 may add to or color the frequency response observed at the transceiver 110 and processed by the processor 116, which affects the accuracy of the determined quantum response of the gas, and thus the accuracy of the atomic clock as a precision clock source. Additionally, Doppler broadening results in less accuracy in identifying a particular frequency of the quantum transition, further affecting the accuracy and stability of the atomic clock as a precision clock source. Thus, in one example, the processor 116 calculates the background-free signal based on the difference in the response of the gas cell 804b that receives an electromagnetic wave in one direction and the response of the gas cell 804a that receives electromagnetic waves in opposite directions (or vice versa). In examples where an electromagnetic coupler is utilized, one of the outputs of the coupler corresponds to the difference between the electromagnetic waves after travel through the gas cells 804a, 804b, and thus generates the background-free signal. As a result, the background and Doppler-induced responses are effectively removed, and a resulting signal is indicative of a background- and Doppler-free quantum response of the gas.

In this description, the term "couple" or "couples" means either an indirect or direct connection. Thus, if a first device couples to a second device, that connection may be through a direct connection or through an indirect connection via other devices and connections. Similarly, a device that is coupled between a first component or location and a second component or location may be through a direct connection or through an indirect connection via other devices and connections. Also, in this description, an element or feature that is "configured to" perform a task or function may be configured (e.g., programmed or structurally designed) at a time of manufacturing by a manufacturer to perform the function and/or may be configurable (or re-configurable) by a user after manufacturing to perform the function and/or other additional or alternative functions. The configuring may be through firmware and/or software programming of the device, through a construction and/or layout of hardware components and interconnections of the device, or a combination thereof. Further, uses of the phrases "ground" or similar in this description include a chassis ground, an Earth ground, a floating ground, a virtual ground, a digital ground, a common ground, and/or any other form of ground connection applicable to, or suitable for, the teachings of this description. Unless otherwise stated, in this description, "about," "approximately," or "substantially" preceding a value means+/−10 percent of the stated value.

Modifications are possible in the described embodiments, and other embodiments are possible, within the scope of the claims.

What is claimed is:

1. A system, comprising:
    first and second gas cells each comprising a respective sealed interior waveguide;
    a first transmit antenna coupled to the first gas cell and configured to provide a first electromagnetic wave to travel in the sealed interior of the first gas cell along a first direction;
    a second transmit antenna coupled to the first gas cell and configured to provide a second electromagnetic wave to travel in the sealed interior of the first gas cell along a second direction opposite the first direction;
    a third transmit antenna coupled to the second gas cell and configured to provide a third electromagnetic wave to travel in the sealed interior of the second gas cell;
    a first receive antenna coupled to the first gas cell and configured to generate a first signal indicative of an amount of energy in the first electromagnetic wave after travel through the first gas cell;
    a second receive antenna coupled to the second gas cell and configured to generate a second signal indicative of an amount of energy in the second electromagnetic wave after travel through the second gas cell; and
    a processor coupled to the first and second receive antennas and configured to calculate a background-free signal based on a difference between the first signal and the second signal.

2. The system of claim 1, wherein the first and second gas cells contain a dipolar gas, and a pressure of the dipolar gas in the first gas cell is approximately equal to a pressure of the dipolar gas in the second gas cell.

3. The system of claim 1, wherein an amount of energy of the second electromagnetic wave is greater than an amount of energy of the first electromagnetic wave.

4. The system of claim 1, further comprising:
    a first transmitter coupled to the first transmit antenna, the first transmitter configured to generate the first electromagnetic wave;
    a second transmitter coupled to the second transmit antenna, the second transmitter configured to generate the second electromagnetic wave; and
    a third transmitter coupled to the third transmit antenna, the third transmitter configured to generate the third electromagnetic wave.

5. The system of claim 1, further comprising:
    a transmitter configured to generate an electromagnetic wave;
    a first directional coupler coupled to the transmitter and to the second transmit antenna, the first directional coupler configured to receive the electromagnetic wave from the transmitter and generate the second electromagnetic wave and an intermediate electromagnetic wave; and
    a second directional coupler coupled to the first directional coupler and to the first and third transmit antennas, the second directional coupler configured to receive the intermediate electromagnetic wave and generate the first and third electromagnetic waves;
    in which an amount of energy of the second electromagnetic wave is greater than an amount of energy of the first electromagnetic wave; and
    in which an amount of energy of the third electromagnetic wave is approximately equal to the amount of energy in the first electromagnetic wave.

6. The system of claim 1, wherein the first and second gas cells are formed using one or more layers of a semiconductor wafer.

7. The system of claim 1, wherein the first and second gas cells are formed using approximately equal dimensions.

8. The system of claim 1, wherein the processor is further configured to calculate a normalized, background-free signal based on the difference between the first signal and the second signal and on a sum of the first signal and the second signal.

9. A system, comprising:
    first and second gas cells each comprising a respective sealed interior waveguide;
    a first transmit antenna coupled to the first gas cell and configured to provide a first electromagnetic wave to travel in the sealed interior of the first gas cell along a first direction;
    a second transmit antenna coupled to the first gas cell and configured to provide a second electromagnetic wave to travel in the sealed interior of the first gas cell along a second direction opposite the first direction;
    a third transmit antenna coupled to the second gas cell and configured to provide a third electromagnetic wave to travel in the sealed interior of the second gas cell; and
    an electromagnetic coupler coupled to the gas cells and configured to:
        receive the first and third electromagnetic waves after travel through the first and second gas cells; and
        generate an electromagnetic wave indicative of a difference between the received first and second electromagnetic waves.

10. The system of claim 9, wherein the first and second gas cells contain a dipolar gas, and a pressure of the dipolar gas in the first gas cell is approximately equal to a pressure of the dipolar gas in the second gas cell.

11. The system of claim 9, wherein an amount of energy of the second electromagnetic wave is greater than an amount of energy of the first electromagnetic wave.

12. The system of claim 9, further comprising a receive antenna coupled to the electromagnetic coupler and configured to generate a first signal indicative of an amount of energy in the electromagnetic wave indicative of the difference.

13. The system of claim 9, wherein the electromagnetic coupler is further configured to generate an electromagnetic wave indicative of a sum of the received first and second electromagnetic waves.

14. The system of claim 13, further comprising:
    a first receive antenna coupled to the electromagnetic coupler and configured to generate a first signal indicative of an amount of energy in the electromagnetic wave indicative of the difference; and a second receive antenna coupled to the electromagnetic coupler and configured to generate a second signal indicative of an amount of energy in the electromagnetic wave indicative of the sum.

15. The system of claim 14, further comprising a processor coupled to the first and second receive antennas and configured to calculate a normalized, background-free signal based on the first signal and the second signal.

16. The system of claim 9, wherein the coupler comprises a rat race coupler.

17. The system of claim 9, wherein the coupler comprises a magic tee coupler.

18. The system of claim 9, further comprising:
a first transmitter coupled to the first transmit antenna, the first transmitter configured to generate the first electromagnetic wave;
a second transmitter coupled to the second transmit antenna, the second transmitter configured to generate the second electromagnetic wave; and
a third transmitter coupled to the third transmit antenna, the third transmitter configured to generate the third electromagnetic wave.

19. The system of claim 9, further comprising:
a transmitter configured to generate an electromagnetic wave;
a first directional coupler coupled to the transmitter and to the second transmit antenna, the first directional coupler configured to receive the electromagnetic wave from the transmitter and generate the second electromagnetic wave and an intermediate electromagnetic wave; and
a second directional coupler coupled to the first directional coupler and to the first and third transmit antennas, the second directional coupler configured to receive the intermediate electromagnetic wave and generate the first and third electromagnetic waves;
in which an amount of energy of the second electromagnetic wave is greater than an amount of energy of the first electromagnetic wave; and
in which an amount of energy of the third electromagnetic wave is approximately equal to the amount of energy in the first electromagnetic wave.

20. A method, comprising:
providing a first electromagnetic wave to travel in a sealed interior waveguide of a first gas cell along a first direction;
providing a second electromagnetic wave to travel in the sealed interior of the first gas cell along a second direction opposite the first direction;
providing a third electromagnetic wave to travel in a sealed interior waveguide of a second gas cell;
receiving the first and third electromagnetic waves after travel through the first and second gas cells; and
generating a background-free signal based on a difference between the first and third electromagnetic waves.

* * * * *